US007091316B2

(12) United States Patent
Uchida et al.

(10) Patent No.: US 7,091,316 B2
(45) Date of Patent: Aug. 15, 2006

(54) PROTEIN INDUCED BY HOMOGENEOUS BLOOD TRANSFUSION AND DNA ENCODING THE SAME

(75) Inventors: Hiroo Uchida, Koshigaya (JP); Hirokazu Tanaka, Kyoto (JP); Yasuhiko Kitoh, Kyoto (JP); Akio Fujimura, Tochigi (JP); Eiji Kobayashi, Tochigi (JP)

(73) Assignee: Maruho Co., Ltd., Osaka (JP)

( * ) Notice: Subject to any disclaimer, the term of this patent is extended or adjusted under 35 U.S.C. 154(b) by 243 days.

(21) Appl. No.: 10/344,307

(22) PCT Filed: Aug. 1, 2001

(86) PCT No.: PCT/JP01/06620

§ 371 (c)(1),
(2), (4) Date: Feb. 6, 2003

(87) PCT Pub. No.: WO02/12495

PCT Pub. Date: Feb. 14, 2002

(65) Prior Publication Data

US 2005/0049189 A1 Mar. 3, 2005

(30) Foreign Application Priority Data

Aug. 9, 2000 (JP) ............................ 2000-241169

(51) Int. Cl.
*C07K 1/00* (2006.01)
*A61K 38/00* (2006.01)

(52) U.S. Cl. ........................................ 530/350; 514/12

(58) Field of Classification Search ................ 530/350; 424/85.2

See application file for complete search history.

(56) References Cited

U.S. PATENT DOCUMENTS 5,972,369 A * 10/1999 Roorda et al. .............. 424/424

FOREIGN PATENT DOCUMENTS

WO WO 95/10526 A1 4/1995

OTHER PUBLICATIONS

Nishimura et al., cDNA and deduced amino acid sequence of human PK-120, a plasma kallikrein-sensitive glycoprotein, FEBS Letters, (1995), 357, p. 207-211.*

Eiji Kobayashi, et al., "(3) Endogenous immunosuppressive substances induced by blood transfusion," Japanese Journal of Transfusion Medicine, vol. 45, No. 6, 45 (6), 1999 pp. 783.

Hiroo Uchida, et al., "Characterization of humoral immunosuppressive factors induced after allogeneic blood transfusion and their application for organ transplantation," Japanese Journal of Clinical Immunology, vol. 23 (6), Dec. 2000, pp. 627-629.

G. Opelz, "Comparison of Random Transfusions With Donor-Specific Transfusions for Pretreatment of HLA One-Haplotype-Matched Related Donor Kidney Transplant Recipients, Transplantation Proceedings," vol. XVII, No. 6 (Dec.), 1985, pp. 2357-2361.

Anatolij Horuzsko, et al., "Non-cytotoxic blocking antibodies and suppressor cells induced by donor-specific transfusions in healthy volunteers and potential kidney transplant recipients," Immunology Letters, 26 (1990) pp. 127-130.

Gerhard Opelz, et al., "Poor Kidney-Transplant Survival in Recipients With Frozen-Blood Transfusions or No Transfusions," The Lancet, Sep. 21, 1974, pp. 696-698.

Hector Marino, et al., "Experimental Skin Homografts; Effect of Homohemotherapy on Their Survival Time," American Journal of Surgery, vol. 95, Feb. 1958, pp. 267-273.

R. L. Marquet, et al., "Specific Inhibition of Organ Allograft Rejection by Donor Blood," Transplantation Proceedings, vol. III, No. 1 (Mar.), 1971, pp. 708-710.

J.W. Fabre, et al., "The Effect of Donor Strain Blood Pretreatment on Renal Allograft Rejection in Rats," Transplantation, vol. 14, No. 5, Nov. 1972, pp. 608-615.

David Cranston, et al., "Abrogation of the Immunosuppressive Effect of Donor Spleen Cells on Renal Allografts in the Rat by Irradiation or Heat Treatment," Transplantation, vol. 42, No. 3, Sep. 1986, pp. 302-306.

Margaret J. Dallman, et al., "Peripheral Tolerance to Alloantigen Results from Altered Regulation of the Interleukin 2 Pathway," J. Exp. Med. vol. 173, Jan. 1991, pp. 79-87.

P. S. Nagarkatti, et al., "Induction of Antibodies by Blood Transfusions Capable of Inhibiting Responses in MLC," Transplantation, vol. 36, No. 6, Dec. 1983, pp. 695-699.

William E. Downey III, et al., "Association of Donor-Specific Blood Transfusion Enhancement of Rat Renal Allografts With Accelerated Development of Antiidiotypic Antibodies and Reduced Alloantibody Responses," Transplantation, vol. 49, No. 1, Jan. 1990, pp. 160-166.

William M. Baldwin III, et al., "IgM and IgG Alloantibody Production by Splenocytes and Deposition in Rat Renal Allografts are Decreased by Donor-Specific Blood Transfusion," Transplantation, vol. 51, No. 2, Feb. 1991, pp. 481-485.

(Continued)

*Primary Examiner*—Maryam Monshipouri
*Assistant Examiner*—Agnes Rooke
(74) *Attorney, Agent, or Firm*—Knobbe, Martens, Olson & Bear LLP

(57) ABSTRACT

The present invention relates to a novel protein (MAY-I) which exhibits immunosuppressive activity in allogeneic mixed lymphocyte reaction, and provides a gene encoding that protein, a vector containing said gene, a transformant produced by said vector, a method of manufacturing the said protein with immune activity by culturing said transformant, and a medicinal composition and the like containing the said protein.

5 Claims, 11 Drawing Sheets

OTHER PUBLICATIONS

Hitoshi Nishimura, et al., "cDNA and deduced amino acid sequence of human PK-120, a plasma kallikrein-sensitive glycoprotein," FEBS Letters, 357, 1995, pp. 207-211.

E. Soury, et al., "The H4P Heavy Chain of Inter-α-inhibitor Family Largely Differs in the Structure and Synthesis of Its Prolin-Rich Region from Rat to Human," Biochemical and Biophysical Research Communications, 243, 1998, pp. 522-530.

Ken Hashimoto, et al., "Primary Structure of the Pig Homologue of Human IHRP: Inter-α-Trypsin Inhibitor Family Heavy Chain-Related Protein," J. Biochem., 119, 1996, pp. 577-584.

Ken-ichi Saguchi, et al., "Cloning and Characterization of cDNA for Inter-α-Trypsin Inhibitor Family Heavy Chain-Related Protein (IHRP), a Novel Human Plasma Glycoprotein,"J. Biochem., 117, 1995, pp. 14-18.

Choi-Miura N. H., et al., "Purification and Characterization of a Novel Glycoprotein Which Has Significant Homology to Heavy Chains of Inter-α-Trypsin Inhibitor Family from Human Plasma," J. Biochem., vol. 117, No. 2, 1995, pp. 400-407.

Gonzalez-Ramon, N., et al., "The Major Acute Serum Protein in Pigs in Homologous to Human Plasma Kallikrein Sensitive PK-120," FEBS Letters, vol. 371, No. 3 (1995) pp. 227-230.

Cai, Tao, et al., "Identification of mouse *itih*-4 encoding a glycoprotein with two EF-hand motifs from early embryonic liver," Biochemica et Biophysica Acta, vol. 1398, No. 1 (1998) pp. 32-37.

Pineiro, Matilde, et al., "ITIH4 Serum Concentration Increases during Acute-Phase Processes in Human Patients and Is Up-Regulated by Interleukin-6 in Hepatocarcinoma HepG2 Cells," Biochemical and Biophysical Research Communications, Academic Press Inc., vol. 263 (1999) pp. 224-229.

Gonzalez-Ramon, N., et al., "Pig MAP/ITIH4 and haptoglobin are interleukin-6-dependent acute-phase plasma proteins in porcine primary cultured hepatocytes," European Journal of Biochemistry, vol. 267 (2000) pp. 1878-1885.

Choi-Miura, N.-H., et al., "The novel acute phase protein, IHRP, inhibits actin polymerization and phagocytosis of polymorphonuclear cells," Inflammation Research, vol. 49, No. 6 (2000) pp. 305-310.

Nikolic, Goran, et al., "Acute Phase Profile of Novel Plasma Protein sgp120 (PK-120)," Immunoregulation in Health and Disease, (1997) pp. 235-242.

Uchida, H., et al., "Mechanisms of Immunomodulation Induced by Blood Transfusion: Identification of Humoral Factors," Transplantation Proceedings, vol. 32, No. 2 (2000) pp. 255-256.

* cited by examiner

1. Stimulus cells + Reaction cells 2. 1 + Fraction not binding to Protein G Affinity Column 1. Fr. 28

2. Molecular weight marker

SEQUENCE LISTING

```
<160> NUMBER OF SEQ ID NOS: 30

<210> SEQ ID NO 1
<211> LENGTH: 234
<212> TYPE: PRT
<213> ORGANISM: rat

<400> SEQUENCE: 1

Val Leu Asp Leu Pro Ser Leu Ser Ser Gln Asp Pro Ala Gly Pro Ser
  1               5                  10                  15

Leu Ala Met Leu Pro Lys Val Val Glu Gln Glu Gly Thr Thr Pro Glu
             20                  25                  30

Glu Ser Pro Asn Pro Asp His Pro Arg Ala Pro Thr Ile Ile Leu Pro
         35                  40                  45

Leu Pro Gly Ser Gly Val Asp Gln Leu Cys Val Asp Ile Leu His Ser
     50                  55                  60

Glu Lys Pro Met Lys Leu Phe Val Asp Ile Asn Gln Gly Leu Glu Val
 65                  70                  75                  80
```

-continued

```
Val Gly Lys Tyr Glu Lys Asn Ile Gly Phe Ser Trp Ile Glu Val Thr
                 85                  90                  95

Ile Leu Lys Pro His Leu Gln Val His Ala Thr Pro Glu Arg Leu Val
            100                 105                 110

Val Thr Arg Gly Arg Lys Asn Ser Glu Tyr Lys Trp Lys Lys Thr Leu
        115                 120                 125

Phe Ser Val Leu Pro Gly Leu Lys Met Thr Met Asp Lys Thr Gly Leu
    130                 135                 140

Leu Gln Leu Ser Gly Pro Asp Lys Val Thr Ile Ser Leu Leu Ser Leu
145                 150                 155                 160

Asp Asp Pro Gln Arg Gly Leu Met Leu Leu Leu Asn Asp Thr His His
                165                 170                 175

Phe Ser Asn Asp Ile Thr Gly Glu Leu Gly Gln Phe Tyr Gln Asp Ile
            180                 185                 190

Ile Trp Asp Asp Thr Lys Gln Thr Val Arg Val Leu Gly Ile Asp Tyr
        195                 200                 205

Pro Ala Thr Arg Glu Leu Lys Leu Ser Tyr Gln Asp Gly Phe Pro Gly
    210                 215                 220

Thr Glu Ile Ser Cys Trp Thr Val Lys Ile
225                 230


<210> SEQ ID NO 2
<211> LENGTH: 702
<212> TYPE: DNA
<213> ORGANISM: rat

<400> SEQUENCE: 2

gtgctagacc tgccatcctt atcctcacaa gatccagccg gcccaagtct agccatgtta      60

ccgaaagtgg tggaacaaga aggcaccaca ccagaggaat ccccaaaccc agaccacccc     120

cgggctccta ccatcatcct gccgcttccg ggatctggtg tggaccagct ctgtgtggat     180

atcttacatt ctgagaagcc catgaagctg tttgtagaca tcaatcaggg gctggaggtg     240

gttggcaagt atgagaagaa tatcgggttc tcatggatcg aagtgaccat cctgaagcct     300

cacctgcagg tccatgcaac gcctgaacga ctggtggtga caaggggccg aaaaaactct     360

gaatacaagt ggaagaagac actgttctct gtgttacctg gcttaaagat gaccatggat     420

aagacgggac tgctacagct cagtggccca gacaaagtca ccatcagcct cttgtctctg     480

gatgaccctc agagaggact catgctgctt ttgaatgaca ctcatcactt ctccaacgac     540

attacagggg agcttggtca gttttaccag gatatcatct gggatgatac aaaacagaca     600

gtcagagttc taggaatcga ctacccggct accagagagc tcaagttgag ttatcaagac     660

gggttcccgg gaacagagat ttcctgctgg acggtgaaga ta                        702


<210> SEQ ID NO 3
<211> LENGTH: 27
<212> TYPE: PRT
<213> ORGANISM: rat

<400> SEQUENCE: 3

Val Leu Asp Leu Pro Ser Leu Ser Ser Gln Asp Pro Ala Gly Pro Ser
  1               5                  10                  15

Leu Ala Met Leu Pro Lys Val Val Glu Gln Glu
            20                  25


<210> SEQ ID NO 4
<211> LENGTH: 5
```

-continued

```
<212> TYPE: PRT
<213> ORGANISM: rat

<400> SEQUENCE: 4

Asn Ile Gly Phe Ser
  1               5


<210> SEQ ID NO 5
<211> LENGTH: 4
<212> TYPE: PRT
<213> ORGANISM: rat

<400> SEQUENCE: 5

Gln Thr Val Arg
  1


<210> SEQ ID NO 6
<211> LENGTH: 932
<212> TYPE: PRT
<213> ORGANISM: rat

<400> SEQUENCE: 6

Met Lys Ser Pro Ala Pro Ala His Met Trp Asn Ile Val Leu Val Leu
  1               5                  10                  15

Leu Ser Leu Leu Ala Val Leu Pro Ile Thr Thr Thr Glu Lys Asn Gly
             20                  25                  30

Ile Asp Ile Tyr Ser Leu Thr Val Asp Ser Arg Val Ser Ser Arg Phe
         35                  40                  45

Ala His Thr Val Val Thr Ser Arg Val Val Asn Arg Ala Asp Thr Val
     50                  55                  60

Gln Glu Ala Thr Phe Gln Val Glu Leu Pro Arg Lys Ala Phe Ile Thr
 65                  70                  75                  80

Asn Phe Ser Met Ile Ile Asp Gly Val Thr Tyr Pro Gly Leu Ser Lys
                 85                  90                  95

Arg Arg Leu Lys Pro Glu Ala Ile His Cys Cys Cys Gly Arg Gly Glu
            100                 105                 110

Ser Ala Gly Leu Val Lys Thr Thr Gly Arg Lys Thr Glu Gln Phe Glu
        115                 120                 125

Val Ser Val Asn Val Ala Pro Gly Ser Lys Thr Thr Phe Glu Leu Ile
    130                 135                 140

Tyr Gln Glu Leu Leu Gln Arg Arg Leu Gly Met Tyr Glu Leu Leu Leu
145                 150                 155                 160

Lys Val Arg Pro Glu Gln Leu Val Lys His Leu Gln Met Thr Ser Thr
                165                 170                 175

Ser Leu Ser Pro Gln Gly Ile Ser Thr Leu Glu Thr Glu Ser Thr Phe
            180                 185                 190

Met Thr Gln Glu Leu Ala Asn Ala Leu Thr Thr Ser Gln Asn Lys Thr
        195                 200                 205

Lys Ala His Ile Gln Phe Lys Pro Thr Leu Ser Gln Gln Arg Lys Ser
    210                 215                 220

Gln Asn Glu Gln Asp Thr Val Leu Asp Gly Asp Phe Thr Val Arg Tyr
225                 230                 235                 240

Asp Val Asp Arg Ser Ser Thr Gly Gly Tyr Leu Gln Ile Glu Asn Gly
                245                 250                 255

Tyr Phe Val His His Phe Ala Pro Glu Asp Leu Pro Thr Met Ala Lys
            260                 265                 270

Asn Val Leu Phe Val Ile Asp Lys Ser Gly Ser Met Ala Gly Lys Lys
```

-continued

```
        275                 280                 285

Ile Gln Gln Thr Arg Glu Ala Leu Ile Lys Ile Leu Lys Asp Leu Ser
    290                 295                 300

Thr Gln Asp Gln Phe Asn Ile Ile Val Phe Ser Gly Glu Ala Asn Gln
305                 310                 315                 320

Trp Glu Gln Leu Leu Val Gln Ala Thr Glu Glu Asn Leu Asn Arg Ala
                325                 330                 335

Val Asp Tyr Ala Ser Lys Ile Pro Ala Gln Gly Gly Thr Asn Ile Asn
            340                 345                 350

Lys Ala Val Leu Ser Ala Val Glu Leu Leu Asp Lys Ser Asn Gln Ala
        355                 360                 365

Glu Leu Leu Pro Ser Lys Ser Val Ser Leu Ile Ile Leu Leu Thr Asp
    370                 375                 380

Gly Glu Pro Thr Val Gly Glu Thr Asn Pro Lys Ile Ile Gln Lys Asn
385                 390                 395                 400

Thr Gln Glu Ala Ile Asn Gly Arg Tyr Ser Leu Phe Cys Leu Gly Phe
                405                 410                 415

Gly Phe Asp Val Asn Tyr Pro Phe Leu Glu Lys Leu Ala Leu Asp Asn
            420                 425                 430

Gly Gly Leu Ala Arg Arg Ile Tyr Glu Asp Ser Asp Ser Ala Leu Gln
        435                 440                 445

Leu Gln Asp Phe Tyr Gln Glu Val Ala Asn Pro Leu Leu Ser Ser Val
    450                 455                 460

Thr Phe Glu Tyr Pro Ser Asn Ala Val Glu Asp Val Thr Arg Tyr Asn
465                 470                 475                 480

Phe Gln His His Phe Lys Gly Ser Glu Met Val Val Ala Gly Lys Leu
                485                 490                 495

Arg Asp Gln Gly Pro Asp Val Leu Leu Ala Lys Val Ser Gly Gln Met
            500                 505                 510

His Leu Gln Asn Ile Thr Phe Gln Thr Glu Ala Ser Ile Ala Gln Gln
        515                 520                 525

Glu Lys Glu Phe Gln Gly Pro Lys Tyr Ile Phe His Asn Phe Met Glu
    530                 535                 540

Arg Leu Trp Ala Leu Leu Thr Ile Gln Gln Gln Leu Glu Gln Arg Ile
545                 550                 555                 560

Ser Ala Ser Gly Ala Glu Leu Glu Ala Leu Glu Ala Gln Val Leu Asn
                565                 570                 575

Leu Ser Leu Lys Tyr Asn Phe Val Thr Pro Leu Thr His Met Val Val
            580                 585                 590

Thr Lys Pro Glu Asp Gln Glu Gln Phe Gln Val Ala Glu Lys Pro Thr
        595                 600                 605

Glu Val Asp Gly Gly Val Trp Ser Ile Leu Ser Ala Val Gln Arg His
    610                 615                 620

Phe Lys Thr Pro Thr Thr Gly Ser Lys Leu Leu Thr Ser Arg Leu Arg
625                 630                 635                 640

Gly Asn Arg Phe Gln Thr Leu Ser Arg Leu Gly Asp Gly Leu Val Gly
                645                 650                 655

Ser Arg Gln Tyr Met Pro Pro Pro Gly Leu Pro Gly Pro Pro Gly Leu
            660                 665                 670

Pro Gly Pro Pro Gly Pro Pro Gly His Pro His Phe Ala Ser Ser Ile
        675                 680                 685

Asp Tyr Gly Arg Gln Pro Ser Leu Gly Arg Val Leu Asp Leu Pro Ser
    690                 695                 700
```

-continued

```
Leu Ser Ser Gln Asp Pro Ala Gly Pro Ser Leu Ala Met Leu Pro Lys
705                 710                 715                 720

Val Val Glu Gln Glu Gly Thr Thr Pro Glu Glu Ser Pro Asn Pro Asp
                725                 730                 735

His Pro Arg Ala Pro Thr Ile Ile Leu Pro Leu Pro Gly Ser Gly Val
            740                 745                 750

Asp Gln Leu Cys Val Asp Ile Leu His Ser Glu Lys Pro Met Lys Leu
        755                 760                 765

Phe Val Asp Ile Asn Gln Gly Leu Glu Val Val Gly Lys Tyr Glu Lys
    770                 775                 780

Asn Ile Gly Phe Ser Trp Ile Glu Val Thr Ile Leu Lys Pro His Leu
785                 790                 795                 800

Gln Val His Ala Thr Pro Glu Arg Leu Val Val Thr Arg Gly Arg Lys
                805                 810                 815

Asn Ser Glu Tyr Lys Trp Lys Lys Thr Leu Phe Ser Val Leu Pro Gly
            820                 825                 830

Leu Lys Met Thr Met Asp Lys Thr Gly Leu Leu Gln Leu Ser Gly Pro
        835                 840                 845

Asp Lys Val Thr Ile Ser Leu Leu Ser Leu Asp Asp Pro Gln Arg Gly
    850                 855                 860

Leu Met Leu Leu Leu Asn Asp Thr His His Phe Ser Asn Asp Ile Thr
865                 870                 875                 880

Gly Glu Leu Gly Gln Phe Tyr Gln Asp Ile Ile Trp Asp Asp Thr Lys
                885                 890                 895

Gln Thr Val Arg Val Leu Gly Ile Asp Tyr Pro Ala Thr Arg Glu Leu
            900                 905                 910

Lys Leu Ser Tyr Gln Asp Gly Phe Pro Gly Thr Glu Ile Ser Cys Trp
        915                 920                 925

Thr Val Lys Ile
    930


<210> SEQ ID NO 7
<211> LENGTH: 2958
<212> TYPE: DNA
<213> ORGANISM: rat

<400> SEQUENCE: 7

acgaactgga gacaaatgaa gagccctgcc cctgcccaca tgtggaacat tgtactggtc     60

ttgctctcgc tgttggctgt gcttccgatc actactactg agaagaatgg catcgatatc    120

tacagtctca cagtggactc ccgggtctct tcccgatttg ctcatactgt tgttaccagc    180

cgggtggtca acagagccga tactgttcaa gaagcgacct tccaagtaga gctacccagg    240

aaagccttca tcaccaactt ctccatgatc attgatggtg tgacctaccc agggttgtca    300

aagagaaggc tgaagccaga agcaatacac tgctgctgtg gccggggaga gagcgctggc    360

cttgtcaaga ccactgggag aaagacagag cagtttgaag tgtcagtcaa cgtggcccct    420

ggttccaaga ctaccttcga actcatatac caagagctgc tccaaagacg gctgggaatg    480

tatgagctac tcctcaaagt gaggcctgag cagctggtca agcaccttca gatgacatct    540

acatctttga gccctcaggg tatcagcacc ctggagacag agagtacttt catgacccag    600

gagttggcaa atgcccttac cacttcacag aacaagacca aggcacatat ccagttcaag    660

ccgacactct cccagcaacg gaagtctcag aatgagcagg acacggtgct agatggggat    720

ttcaccgttc gctatgatgt ggaccggtct tccactggcg gatacttca gattgagaac    780
```

-continued

```
ggctactttg tgcaccactt tgccccagag gaccttccta caatggccaa gaatgtgctc    840
tttgtcattg ataaaagcgg atctatggca ggcaagaaaa tccaacagac ccgagaagcc    900
ctaatcaaga tcttgaaaga cctcagcacc caagaccagt tcaatatcat tgtgttcagt    960
ggggaagcaa accagtggga gcagttgctg gtgcaagcaa cagaagagaa cttgaacagg   1020
gcggttgact atgcttccaa gatcccggct cagggaggga ccaacatcaa taaagcagtg   1080
ctatcggctg tggaactgct ggataaaagc aaccaggctg agctactgcc ctccaagagc   1140
gtttccctca tcatcctgct cacggatggc gagcccactg tgggggagac caatcccaag   1200
attatccaga agaacacaca ggaagccatc aatgggcggt atagcctctt ctgcctgggg   1260
tttggctttg atgtgaacta tcctttcctg gagaagctgg ccctggacaa cggaggcctg   1320
gcccggcgca tctacgagga ctcagactct gctctgcagc ttcaggactt ctaccaggaa   1380
gtggccaatc cgctgctgtc atcagtgacc tttgaatatc ccagcaatgc tgtggaggac   1440
gtcacgcggt acaacttcca acaccacttt aagggctcag agatggtggt ggctgggaag   1500
ctccgggacc agggccctga tgtcctctta gccaaagtca gtgggcagat gcacctgcag   1560
aacatcactt tccaaacgga ggccagcata gcccaacaag agaaagagtt ccagggtcct   1620
aagtacatct ttcataactt tatggagaga ctctgggcgt tgctgaccat acagcaacag   1680
ctggagcaga ggatttcagc ctcaggagct gagttagagg ccctcgaggc ccaagttctg   1740
aacttgtcac tcaagtacaa ttttgtcact cctctcacgc acatggtggt caccaaacct   1800
gaagatcaag aacaattcca agttgctgag aagcctacgg aagtcgatgg tggagtgtgg   1860
agtatcctct cagcagttca acggcatttc aagactccta ccacaggatc taaactgctg   1920
acatccaggc tgagaggaaa taggttccag acattgtcca gactcgggga tggtctcgtt   1980
ggatctagac aatacatgcc tcctcctgga cttcctggac ctcctggact tcctggacct   2040
cctgggcctc ccggacatcc tcattttgct tctagcattg actacggcag gcagccttcc   2100
ttgggaaggg tgctagacct gccatcctta tcctcacaag atccagccgg cccaagtcta   2160
gccatgttac cgaaagtggt ggaacaagaa ggcaccacac cagaggaatc cccaaaccca   2220
gaccaccccc gggctcctac catcatcctg ccgcttccgg gatctggtgt ggaccagctc   2280
tgtgtggata tcttacattc tgagaagccc atgaagctgt ttgtagacat caatcagggg   2340
ctggaggtgg ttggcaagta tgagaagaat atcgggttct catggatcga agtgaccatc   2400
ctgaagcctc acctgcaggt ccatgcaacg cctgaacgac tggtggtgac aaggggccga   2460
aaaaactctg aatacaagtg gaagaagaca ctgttctctg tgttacctgg cttaaagatg   2520
accatggata agacgggact gctacagctc agtggcccag acaaagtcac catcagcctc   2580
ttgtctctgg atgaccctca gagaggactc atgctgcttt tgaatgacac tcatcacttc   2640
tccaacgaca ttacagggga gcttggtcag ttttaccagg atatcatctg ggatgataca   2700
aaacagacag tcagagttct aggaatcgac tacccggcta ccagagagct caagttgagt   2760
tatcaagacg ggttcccggg aacagagatt tcctgctgga cggtgaagat atagaactga   2820
caggagcatt gtttgctacc tgccatgttg tcctcgtatg caggcggatg acactgtgtg   2880
ccaacagggc cgcctgtgag gcctagacct tgatggggaa gaggatgctc tcttgttaca   2940
aataaagaag ggtgatgt                                                 2958
```

<210> SEQ ID NO 8
<211> LENGTH: 933
<212> TYPE: PRT

-continued

<213> ORGANISM: rat

<400> SEQUENCE: 8

```
Met Lys Ser Pro Ala Pro Ala His Met Trp Asn Ile Val Leu Val Leu
  1               5                  10                  15

Leu Ser Leu Leu Ala Val Leu Pro Ile Thr Thr Thr Glu Lys Asn Gly
             20                  25                  30

Ile Asp Ile Tyr Ser Leu Thr Val Asp Ser Arg Val Ser Ser Arg Phe
         35                  40                  45

Ala His Thr Val Val Thr Ser Arg Val Val Asn Arg Ala Asp Thr Val
     50                  55                  60

Gln Glu Ala Thr Phe Gln Val Glu Leu Pro Arg Lys Ala Phe Ile Thr
 65                  70                  75                  80

Asn Phe Ser Met Ile Ile Asp Gly Val Thr Tyr Pro Gly Val Val Leu
                 85                  90                  95

Glu Lys Ala Glu Ala Gln Lys Gln Tyr Tyr Ala Ala Val Gly Arg Gly
            100                 105                 110

Glu Ser Ala Gly Leu Val Lys Thr Thr Gly Arg Lys Thr Glu Gln Phe
        115                 120                 125

Glu Val Ser Val Asn Val Ala Pro Gly Ser Lys Thr Thr Phe Glu Leu
    130                 135                 140

Ile Tyr Gln Glu Leu Leu Gln Arg Arg Leu Gly Met Tyr Glu Leu Leu
145                 150                 155                 160

Leu Lys Val Arg Pro Glu Gln Leu Val Lys His Leu Gln Met Asp Ile
                165                 170                 175

Tyr Ile Phe Glu Pro Gln Gly Ile Ser Thr Leu Glu Thr Glu Ser Thr
            180                 185                 190

Phe Met Thr Gln Glu Leu Ala Asn Ala Leu Thr Thr Ser Gln Asn Lys
        195                 200                 205

Thr Lys Ala His Ile Gln Phe Lys Pro Thr Leu Ser Gln Gln Arg Lys
    210                 215                 220

Ser Gln Asn Glu Gln Asp Thr Val Leu Asp Gly Asp Phe Thr Val Arg
225                 230                 235                 240

Tyr Asp Val Asp Arg Ser Ser Thr Gly Gly Thr Ile Gln Ile Glu Asn
                245                 250                 255

Gly Tyr Phe Val His His Phe Ala Pro Glu Asp Leu Pro Thr Met Ala
            260                 265                 270

Lys Asn Val Leu Phe Val Ile Asp Lys Ser Gly Ser Met Ala Gly Lys
        275                 280                 285

Lys Ile Gln Gln Thr Arg Glu Ala Leu Ile Lys Ile Leu Lys Asp Leu
    290                 295                 300

Ser Thr Gln Asp Gln Phe Asn Ile Ile Val Phe Ser Gly Glu Ala Asn
305                 310                 315                 320

Gln Trp Glu Gln Leu Leu Val Gln Ala Thr Glu Glu Asn Leu Asn Arg
                325                 330                 335

Ala Val Asp Tyr Ala Ser Lys Ile Pro Ala Gln Gly Gly Thr Asn Ile
            340                 345                 350

Asn Lys Ala Val Leu Ser Ala Val Glu Leu Leu Asp Lys Ser Asn Gln
        355                 360                 365

Ala Glu Leu Leu Pro Ser Lys Ser Val Ser Leu Ile Ile Leu Leu Thr
    370                 375                 380

Asp Gly Glu Pro Thr Val Gly Glu Thr Asn Pro Lys Ile Ile Gln Lys
385                 390                 395                 400
```

-continued

```
Asn Thr Gln Glu Ala Ile Asn Gly Arg Tyr Ser Leu Phe Cys Leu Gly
                405                 410                 415

Phe Gly Phe Asp Val Asn Tyr Pro Phe Leu Glu Lys Leu Ala Leu Asp
            420                 425                 430

Asn Gly Gly Leu Ala Arg Arg Ile Tyr Glu Asp Ser Asp Ser Ala Leu
        435                 440                 445

Gln Leu Gln Asp Phe Tyr Gln Glu Val Ala Asn Pro Leu Leu Ser Ser
    450                 455                 460

Val Thr Phe Glu Tyr Pro Ser Asn Ala Val Glu Asp Val Thr Arg Tyr
465                 470                 475                 480

Asn Phe Gln His His Phe Lys Gly Ser Glu Met Val Val Ala Gly Lys
                485                 490                 495

Leu Arg Asp Gln Gly Pro Asp Val Leu Leu Ala Lys Val Ser Gly Gln
            500                 505                 510

Met His Leu Gln Asn Ile Thr Phe Gln Thr Glu Ala Ser Ile Ala Gln
        515                 520                 525

Gln Glu Lys Glu Phe Gln Gly Pro Lys Tyr Ile Phe His Asn Phe Met
    530                 535                 540

Glu Arg Leu Trp Ala Leu Leu Thr Ile Gln Gln Gln Leu Glu Gln Arg
545                 550                 555                 560

Ile Ser Ala Ser Gly Ala Glu Leu Glu Ala Leu Glu Ala Gln Val Leu
                565                 570                 575

Asn Leu Ser Leu Lys Tyr Asn Phe Val Thr Pro Leu Thr His Met Val
            580                 585                 590

Val Thr Lys Pro Glu Asp Gln Glu Gln Phe Gln Val Ala Glu Lys Pro
        595                 600                 605

Thr Glu Val Asp Gly Gly Val Trp Ser Ile Leu Ser Ala Val Gln Arg
    610                 615                 620

His Phe Lys Thr Pro Thr Thr Gly Ser Lys Leu Leu Thr Ser Arg Leu
625                 630                 635                 640

Arg Gly Asn Arg Phe Gln Thr Leu Ser Arg Leu Gly Asp Gly Leu Val
                645                 650                 655

Gly Ser Arg Gln Tyr Met Pro Pro Pro Gly Leu Pro Gly Pro Pro Gly
            660                 665                 670

Leu Pro Gly Pro Pro Gly Pro Pro Gly His Pro His Phe Ala Ser Ser
        675                 680                 685

Ile Asp Tyr Gly Arg Gln Pro Ser Leu Gly Arg Val Leu Asp Leu Pro
    690                 695                 700

Ser Leu Ser Ser Gln Asp Pro Ala Gly Pro Ser Leu Ala Met Leu Pro
705                 710                 715                 720

Lys Val Val Glu Gln Glu Gly Thr Thr Pro Glu Glu Ser Pro Asn Pro
                725                 730                 735

Asp His Pro Arg Ala Pro Thr Ile Ile Leu Pro Leu Pro Gly Ser Gly
            740                 745                 750

Val Asp Gln Leu Cys Val Asp Ile Leu His Ser Glu Lys Pro Met Lys
        755                 760                 765

Leu Phe Val Asp Ile Asn Gln Gly Leu Glu Val Val Gly Lys Tyr Glu
    770                 775                 780

Lys Asn Ile Gly Phe Ser Trp Ile Glu Val Thr Ile Leu Lys Pro His
785                 790                 795                 800

Leu Gln Val His Ala Thr Pro Glu Arg Leu Val Val Thr Arg Gly Arg
                805                 810                 815

Lys Asn Ser Glu Tyr Lys Trp Lys Lys Thr Leu Phe Ser Val Leu Pro
```

-continued

```
            820                 825                 830

Gly Leu Lys Met Thr Met Asp Lys Thr Gly Leu Leu Gln Leu Ser Gly
        835                 840                 845

Pro Asp Lys Val Thr Ile Ser Leu Leu Ser Leu Asp Asp Pro Gln Arg
    850                 855                 860

Gly Leu Met Leu Leu Leu Asn Asp Thr His His Phe Ser Asn Asp Ile
865                 870                 875                 880

Thr Gly Glu Leu Gly Gln Phe Tyr Gln Asp Ile Ile Trp Asp Asp Thr
                885                 890                 895

Lys Gln Thr Val Arg Val Leu Gly Ile Asp Tyr Pro Ala Thr Arg Glu
            900                 905                 910

Leu Lys Leu Ser Tyr Gln Asp Gly Phe Pro Gly Thr Glu Ile Ser Cys
        915                 920                 925

Trp Thr Val Lys Ile
    930


<210> SEQ ID NO 9
<211> LENGTH: 2961
<212> TYPE: DNA
<213> ORGANISM: rat

<400> SEQUENCE: 9

acgaactgga gacaaatgaa gagccctgcc cctgcccaca tgtggaacat tgtactggtc     60

ttgctctcgc tgttggctgt gcttccgatc actactactg agaagaatgg catcgatatc    120

tacagtctca cagtggactc ccgggtctct tcccgatttg ctcatactgt tgttaccagc    180

cgggtggtca acagagccga tactgttcaa gaagcgacct tccaagtaga gctacccagg    240

aaagccttca tcaccaactt ctccatgatc attgatggtg tgacctaccc aggggttgtc    300

aaagagaagg ctgaagccca gaagcaatac actgctgctg tgggccgggg agagagcgct    360

ggccttgtca agaccactgg gagaaagaca gagcagtttg aagtgtcagt caacgtggcc    420

cctggttcca agactacctt cgaactcata taccaagagc tgctccaaag acggctggga    480

atgtatgagc tactcctcaa agtgaggcct gagcagctgg tcaagcacct tcagatggac    540

atctacatct tgagcctcag ggtatcagc accctggaga cagagagtac tttcatgacc    600

caggagttgg caaatgccct taccacttca cagaacaaga ccaaggcaca tatccagttc    660

aagccgacac tctcccagca acggaagtct cagaatgagc aggacacggt gctagatggg    720

gatttcaccg ttcgctatga tgtggaccgg tcttccactg gcggtaccat tcagattgag    780

aacggctact ttgtgcacca ctttgcccca gaggaccttc ctacaatggc caagaatgtg    840

ctctttgtca ttgataaaag cggatctatg gcaggcaaga aaatccaaca gacccgagaa    900

gccctaatca agatcttgaa agacctcagc acccaagacc agttcaatat cattgtgttc    960

agtggggaag caaaccagtg ggagcagttg ctggtgcaag caacagaaga gaacttgaac   1020

agggcggttg actatgcttc caagatcccg gctcagggag ggaccaacat caataaagca   1080

gtgctatcgg ctgtggaact gctggataaa agcaaccagg ctgagctact gccctccaag   1140

agcgtttccc tcatcatcct gctcacggat ggcgagccca ctgtggggga gaccaatccc   1200

aagattatcc agaagaacac acaggaagcc atcaatgggc ggtatagcct cttctgcctg   1260

gggtttggct ttgatgtgaa ctatcctttc ctggagaagc tggccctgga caacggaggc   1320

ctggcccggc gcatctacga ggactcagac tctgctctgc agcttcagga cttctaccag   1380

gaagtggcca atccgctgct gtcatcagtg acctttgaat atcccagcaa tgctgtggag   1440
```

-continued

```
gacgtcacgc ggtacaactt ccaacaccac tttaagggct cagagatggt ggtggctggg   1500

aagctccggg accagggccc tgatgtcctc ttagccaaag tcagtgggca gatgcacctg   1560

cagaacatca ctttccaaac ggaggccagc atagcccaac aagagaaaga gttccagggt   1620

cctaagtaca tctttcataa ctttatggag agactctggg cgttgctgac catacagcaa   1680

cagctggagc agaggatttc agcctcagga gctgagttag aggccctcga ggcccaagtt   1740

ctgaacttgt cactcaagta caattttgtc actcctctca cgcacatggt ggtcaccaaa   1800

cctgaagatc aagaacaatt ccaagttgct gagaagccta cggaagtcga tggtggagtg   1860

tggagtatcc tctcagcagt tcaacggcat ttcaagactc ctaccacagg atctaaactg   1920

ctgacatcca ggctgagagg aaataggttc cagacattgt ccagactcgg ggatggtctc   1980

gttggatcta gacaatacat gcctcctcct ggacttcctg gacctcctgg acttcctgga   2040

cctcctgggc ctcccggaca tcctcatttt gcttctagca ttgactacgg caggcagcct   2100

tccttgggaa gggtgctaga cctgccatcc ttatcctcac aagatccagc cggcccaagt   2160

ctagccatgt taccgaaagt ggtggaacaa gaaggcacca caccagagga atccccaaac   2220

ccagaccacc cccgggctcc taccatcatc ctgccgcttc cgggatctgg tgtggaccag   2280

ctctgtgtgg atatcttaca ttctgagaag cccatgaagc tgtttgtaga catcaatcag   2340

gggctggagg tggttggcaa gtatgagaag aatatcgggt tctcatggat cgaagtgacc   2400

atcctgaagc ctcacctgca ggtccatgca acgcctgaac gactggtggt gacaaggggc   2460

cgaaaaaact ctgaatacaa gtggaagaag acactgttct ctgtgttacc tggcttaaag   2520

atgaccatgg ataagacggg actgctacag ctcagtggcc cagacaaagt caccatcagc   2580

ctcttgtctc tggatgaccc tcagagagga ctcatgctgc ttttgaatga cactcatcac   2640

ttctccaacg acattacagg ggagcttggt cagttttacc aggatatcat ctgggatgat   2700

acaaaacaga cagtcagagt tctaggaatc gactacccgg ctaccagaga gctcaagttg   2760

agttatcaag acgggttccc gggaacagag atttcctgct ggacggtgaa gatatagaac   2820

tgacaggagc attgtttgct acctgccatg ttgtcctcgt atgcaggcgg atgacactgt   2880

gtgccaacag ggccgcctgt gaggcctaga ccttgatggg gaagaggatg ctctcttgtt   2940

acaaataaag aagggtgatg t                                              2961
```

<210> SEQ ID NO 10
<211> LENGTH: 930
<212> TYPE: PRT
<213> ORGANISM: Homo sapiens

<400> SEQUENCE: 10

```
Met Lys Pro Pro Arg Pro Val Arg Thr Cys Ser Lys Val Leu Val Leu
  1               5                  10                  15

Leu Ser Leu Leu Ala Ile His Gln Thr Thr Thr Ala Glu Lys Asn Gly
             20                  25                  30

Ile Asp Ile Tyr Ser Leu Thr Val Asp Ser Arg Val Ser Ser Arg Phe
         35                  40                  45

Ala His Thr Val Val Thr Ser Arg Val Val Asn Arg Ala Asn Thr Val
     50                  55                  60

Gln Glu Ala Thr Phe Gln Met Glu Leu Pro Lys Lys Ala Phe Ile Thr
 65                  70                  75                  80

Asn Phe Ser Met Asn Ile Asp Gly Met Thr Tyr Pro Gly Ile Ile Lys
                 85                  90                  95

Glu Lys Ala Glu Ala Gln Ala Gln Tyr Ser Ala Ala Val Ala Lys Gly
```

-continued

```
            100                 105                 110

Lys Asn Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
    210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
        275                 280                 285

Lys Ile Gln Gln Thr Arg Glu Ala Leu Ile Lys Ile Leu Asp Asp Leu
    290                 295                 300

Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
        355                 360                 365

Glu Glu Arg Leu Pro Glu Gly Ser Val Ser Leu Ile Ile Leu Leu Thr
    370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
        435                 440                 445

Gln Leu Gln Asp Phe Tyr Gln Glu Val Ala Asn Pro Leu Leu Thr Ala
    450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
        515                 520                 525
```

-continued

```
Gln Glu Ala Glu Phe Gln Ser Pro Lys Tyr Ile Phe His Asn Phe Met
    530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
        595                 600                 605

Met Glu Gly Glu Ser Arg Asn Arg Asn Val His Ser Gly Ser Thr Phe
    610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
            660                 665                 670

Pro Gly Pro Pro Asp Val Pro Asp His Ala Ala Tyr His Pro Phe Arg
        675                 680                 685

Arg Leu Ala Ile Leu Pro Ala Ser Ala Pro Pro Ala Thr Ser Asn Pro
    690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
    770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
        835                 840                 845

Phe Trp Asp Gly Arg Gly Glu Gly Leu Arg Leu Leu Leu Arg Asp Thr
    850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr
                885                 890                 895

Leu Arg Val Gln Gly Asn Asp His Ser Ala Thr Arg Glu Arg Arg Leu
            900                 905                 910

Asp Tyr Gln Glu Gly Pro Pro Gly Val Glu Ile Ser Cys Trp Ser Val
        915                 920                 925

Glu Leu
    930
```

-continued

<210> SEQ ID NO 11
<211> LENGTH: 2963
<212> TYPE: DNA
<213> ORGANISM: Homo sapiens

<400> SEQUENCE: 11
gtgagaagcc tcctggcaga cactggagcc acgatgaagc ccccaaggcc tgtccgtacc 60
tgcagcaaag ttctcgtcct gctttcactg ctggccatcc accagaccac tactgccgaa 120
aagaatggca tcgacatcta cagcctcacc gtggactcca gggtctcatc ccgatttgcc 180
cacacggtcg tcaccagccg agtggtcaat agggccaata cggtacagga ggccaccttc 240
cagatggagc tgcccaagaa agccttcatc accaacttct ccatgaacat cgatggcatg 300
acctacccag ggatcatcaa ggagaaggct gaagcccagg cacagtacag cgcagcagtg 360
gccaagggaa agaacgctgg cctcgtcaag gccaccggga gaaacatgga gcagttccag 420
gtgtcggtca gtgtggctcc caatgccaag atcacctttg agctggtcta tgaggagctg 480
ctcaagcggc gtttgggggt gtacgagctg ctgctgaaag tgcggcccca gcagctggtc 540
aagcacctgc agatggacat tcacatcttc gagccccagg gcatcagctt tctggagaca 600
gagagcacct tcatgaccaa ccagctggta gacgccctca ccacctggca gaataagacc 660
aaggctcaca tccggttcaa gccaacactt tcccagcagc aaaagtcccc agagcagcaa 720
gaaacagtcc tggacggcaa cctcattatc cgctatgatg tggaccgggc catctccggg 780
ggctccattc agatcgagaa cggctacttt gtacactact ttgcccccga gggcctaacc 840
acaatgccca agaatgtggt ctttgtcatt gacaagagcg gctccatgag tggcaggaaa 900
atccagcaga cccgggaagc cctaatcaag atcctggatg acctcagccc cagagaccag 960
ttcaacctca tcgtcttcag tacagaagca actcagtgga ggccatcact ggtgccagcc 1020
tcagccgaga acgtgaacaa ggccaggagc tttgctgcgg gcatccaggc cctgggaggg 1080
accaacatca atgatgcaat gctgatggct gtgcagttgc tggacagcag caaccaggag 1140
gagcggctgc ccgaagggag tgtctcactc atcatcctgc tcaccgatgg cgaccccact 1200
gtgggggaga ctaaccccag gagcatccag aataacgtgc gggaagctgt aagtggccgg 1260
tacagcctct tctgcctggg cttcggtttc gacgtcagct atgccttcct ggagaagctg 1320
gcactggaca atggcggcct ggcccggcgc atccatgagg actcagactc tgccctgcag 1380
ctccaggact tctaccagga agtggccaac ccactgctga cagcagtgac cttcgagtac 1440
ccaagcaatg ccgtggagga ggtcactcag aacaacttcc ggctcctctt caagggctca 1500
gagatggtgg tggctgggaa gctccaggac cgggggcctg atgtgctcac agccacagtc 1560
agtgggaagc tgcctacaca gaacatcact ttccaaacgg agtccagtgt ggcagagcag 1620
gaggcggagt tccagagccc caagtatatc ttccacaact tcatggagag gctctgggca 1680
tacctgacta tccagcagct gctggagcaa actgtctccg catccgacgc tgatcagcag 1740
gccctccgga accaagcgct gaatttatca cttgcctaca gctttgtcac gcctctcaca 1800
tctatggtag tcaccaaacc cgatgaccaa gagcagtctc aagttgctga gaagcccatg 1860
gaaggcgaaa gtagaaacag gaatgtccac tcaggttcca ctttcttcaa atattatctc 1920
cagggagcaa aaataccaaa accagaggct tccttttctc caagaagagg atggaataga 1980
caagctggag ctgctggctc ccggatgaat ttcagacctg ggttctcag ctccaggcaa 2040 cttggactcc caggacctcc tgatgttcct gaccatgctg cttaccaccc cttccgccgt 2100
ctggccatct tgcctgcttc agcaccacca gccacctcaa atcctgatcc agctgtgtct 2160

-continued

```
cgtgtcatga atatgaaaat cgaagaaaca accatgacaa cccaaacccc agcccccata   2220

caggctccct ctgccatcct gccactgcct gggcagagtg tggagcggct ctgtgtggac   2280

cccagacacc gccaggggcc agtgaacctg ctctcagacc ctgagcaagg ggttgaggtg   2340

actggccagt atgagaggga gaaggctggg ttctcatgga tcgaagtgac cttcaagaac   2400

cccctggtat gggttcacgc atcccctgaa cacgtggtgg tgactcggaa ccgaagaagc   2460

tctgcgtaca agtggaagga gacgctattc tcagtgatgc ccggcctgaa gatgaccatg   2520

gacaagacgg gtctcctgct gctcagtgac ccagacaaag tgaccatcgg cctgttgttc   2580

tgggatggcc gtggggaggg gctccggctc cttctgcgtg acactgaccg cttctccagc   2640

cacgttggag ggacccttgg ccagttttac caggaggtgc tctggggatc tccagcagca   2700

tcagatgacg gcagacgcac gctgagggtt cagggcaatg accactctgc caccagagag   2760

cgcaggctgg attaccagga ggggcccccg ggagtggaga tttcctgctg gtctgtggag   2820

ctgtagttct gatggaagga gctgtgccca ccctgtacac ttggcttccc cctgcaactg   2880

cagggccgct tctggggcct ggaccaccat ggggaggaag agtcccactc attacaaata   2940

aagaaaggtg gtgtgagcct ggg                                           2963
```

```
<210> SEQ ID NO 12
<211> LENGTH: 930
<212> TYPE: PRT
<213> ORGANISM: Homo sapiens

<400> SEQUENCE: 12

Met Lys Pro Pro Arg Pro Val Arg Thr Cys Ser Lys Val Leu Val Leu
  1               5                  10                  15

Leu Ser Leu Leu Ala Ile His Gln Thr Thr Thr Ala Glu Lys Asn Gly
             20                  25                  30

Ile Asp Ile Tyr Ser Leu Thr Val Asp Ser Arg Val Ser Ser Arg Phe
         35                  40                  45

Ala His Thr Val Val Thr Ser Arg Val Val Asn Arg Ala Asn Thr Val
     50                  55                  60

Gln Glu Ala Thr Phe Gln Met Glu Leu Pro Lys Lys Ala Phe Ile Thr
 65                  70                  75                  80

Asn Phe Ser Met Ile Ile Asp Gly Met Thr Tyr Pro Gly Ile Ile Lys
                 85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
    210                 215                 220
```

-continued

```
Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
        275                 280                 285

Lys Ile Gln Gln Thr Arg Glu Ala Leu Ile Lys Ile Leu Asp Asp Leu
    290                 295                 300

Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
        355                 360                 365

Glu Glu Arg Leu Pro Glu Gly Ser Val Ser Leu Ile Ile Leu Leu Thr
    370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
        435                 440                 445

Gln Leu Gln Asp Phe Tyr Gln Glu Val Ala Asn Pro Leu Leu Thr Ala
    450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
        515                 520                 525

Gln Glu Ala Glu Phe Gln Ser Pro Lys Tyr Ile Phe His Asn Phe Met
    530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
        595                 600                 605

Met Glu Gly Glu Ser Arg Asn Arg Asn Val His Ser Gly Ser Thr Phe
    610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
```

-continued

```
                645                 650                 655

Arg Met Asn Phe Arg Pro Gly Val Leu Ser Ser Arg Gln Leu Gly Leu
            660                 665                 670

Pro Gly Pro Pro Asp Val Pro Asp His Ala Ala Tyr His Pro Phe Arg
        675                 680                 685

Arg Leu Ala Ile Leu Pro Ala Ser Ala Pro Pro Ala Thr Ser Asn Pro
    690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
    770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
        835                 840                 845

Phe Trp Asp Gly Arg Gly Glu Gly Leu Arg Leu Leu Leu Arg Asp Thr
    850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr
                885                 890                 895

Leu Arg Val Gln Gly Asn Asp His Ser Ala Thr Arg Glu Arg Arg Leu
            900                 905                 910

Asp Tyr Gln Glu Gly Pro Pro Gly Val Glu Ile Ser Cys Trp Ser Val
        915                 920                 925

Glu Leu
    930
```

<210> SEQ ID NO 13
<211> LENGTH: 3058
<212> TYPE: DNA
<213> ORGANISM: Homo sapiens

<400> SEQUENCE: 13

```
gccccacagt gagaggaagg aaggcaacag tcgccagcag ccgatgtgaa gaccggactc      60

cgtgcgcccc tcgccgcctc tgcctggcca catcgatgtt gtgtccgccg cctgctcgcc     120

cggatcacga tgaagccccc aaggcctgtc cgtacctgca gcaaagttct cgtcctgctt     180

tcactgctgg ccatccacca gactactact gccgaaaaga atggcatcga catctacagc     240

ctcaccgtgg actccagggt ctcatcccga tttgcccaca cggtcgtcac cagccgagtg     300

gtcaataggg ccaatactgt gcaggaggcc accttccaga tggagctgcc caagaaagcc     360

ttcatcacca acttctccat gatcatcgat ggcatgacct acccagggat catcaaggag     420

aaggctgaag cccaggcaca gtacagcgca gcagtggcca agggaaagag cgctggcctc     480
```

-continued

```
gtcaaggcca ccgggagaaa catggagcag ttccaggtgt cggtcagtgt ggctcccaat    540
gccaagatca cctttgagct ggtctatgag gagctgctca agcggcgttt gggggtgtac    600
gagctgctgc tgaaagtgcg gccccagcag ctggtcaagc acctgcagat ggacattcac    660
atcttcgagc cccagggcat cagctttctg gagacagaga gcaccttcat gaccaaccag    720
ctggtagacg ccctcaccac ctggcagaat aagaccaagg ctcacatccg gttcaagcca    780
acactttccc agcagcaaaa gtccccagag cagcaagaaa cagtcctgga cggcaacctc    840
attatccgct atgatgtgga ccgggccatc tccgggggct ccattcagat cgagaacggc    900
tactttgtac actactttgc ccccgagggc ctaaccacaa tgcccaagaa tgtggtcttt    960
gtcattgaca agagcggctc catgagtggc aggaaaatcc agcagacccg ggaagcccta   1020
atcaagatcc tggatgacct cagccccaga gaccagttca acctcatcgt cttcagtaca   1080
gaagcaactc agtggaggcc atcactggtg ccagcctcag ccgagaacgt gaacaaggcc   1140
aggagctttg ctgcgggcat ccaggccctg ggagggacca acatcaatga tgcaatgctg   1200
atggctgtgc agttgctgga cagcagcaac caggaggagc ggctgcccga agggagtgtc   1260
tcactcatca tcctgctcac cgatggcgac cccactgtgg gggagactaa ccccaggagc   1320
atccagaata acgtgcggga agctgtaagt ggccggtaca gcctcttctg cctgggcttc   1380
ggtttcgacg tcagctatgc cttcctggag aagctggcac tggacaatgg cggcctggcc   1440
cggcgcatcc atgaggactc agactctgcc ctgcagctcc aggacttcta ccaggaagtg   1500
gccaacccac tgctgacagc agtgaccttc gagtacccaa gcaatgccgt ggaggaggtc   1560
actcagaaca acttccggct cctcttcaag ggctcagaga tggtggtggc tgggaagctc   1620
caggaccggg ggcctgatgt gctcacagcc acagtcagtg ggaagctgcc tacacagaac   1680
atcactttcc aaacggagtc cagtgtggca gagcaggagg cggagttcca gagccccaag   1740
tatatcttcc acaacttcat ggagaggctc tgggcatacc tgactatcca gcagctgctg   1800
gagcaaactg tctccgcatc cgatgctgat cagcaggccc tccggaacca agcgctgaat   1860
ttatcacttg cctacagctt tgtcacgcct ctcacatcta tggtagtcac caaacccgat   1920
gaccaagagc agtctcaagt tgctgagaag cccatggaag gcgaaagtag aaacaggaat   1980
gtccactcag gttccacttt cttcaaatat tatctccagg gagcaaaaat accaaaaacca   2040
gaggcttcct tttctccaag aagaggatgg aatagacaag ctggagctgc tggctcccgg   2100
atgaatttca gacctggggt tctcagctcc aggcaacttg gactcccagg acctcctgat   2160
gttcctgacc atgctgctta ccacccctc cgccgtctgg ccatcttgcc tgcttcagca   2220
ccaccagcca cctcaaatcc tgatccagct gtgtctcgtg tcatgaatat gaaaatcgaa   2280
gaaacaacca tgacaaccca aaccccagcc cccatacagg ctccctctgc catcctgcca   2340
ctgcctgggc agagtgtgga gcggctctgt gtggacccca gacaccgcca ggggccagtg   2400
aacctgctct cagaccctga gcaaggggtt gaggtgactg gccagtatga gagggagaag   2460
gctgggttct catggatcga agtgaccttc aagaaccccc tggtatgggt tcacgcatcc   2520
cctgaacacg tggtggtgac tcggaaccga agaagctctg cgtacaagtg gaaggagacg   2580
ctattctcag tgatgcccgg cctgaagatg accatggaca agacgggtct cctgctgctc   2640
agtgacccag acaaagtgac catcggcctg ttgttctggg atggccgtgg ggaggggctc   2700
cggctccttc tgcgtgacac tgaccgcttc tccagccacg ttggagggac ccttggccag   2760
ttttaccagg aggtgctctg gggatctcca gcagcatcag atgacggcag acgcacgctg   2820
```

-continued

```
agggttcagg gcaatgacca ctctgccacc agagagcgca ggctggatta ccaggagggg   2880

cccccgggag tggagatttc ctgctggtct gtggagctgt agttctgatg gaaggagctg   2940

tgcccaccct gtacacttgg cttccccctg caactgcagg gccgcttctg ggcctggac    3000

caccatgggg aggaagagtc ccactcatta caaataaaga aaggtggtgt gagcctga     3058
```

<210> SEQ ID NO 14
<211> LENGTH: 242
<212> TYPE: PRT
<213> ORGANISM: Homo sapiens

<400> SEQUENCE: 14

```
Arg Leu Ala Ile Leu Pro Ala Ser Ala Pro Pro Ala Thr Ser Asn Pro
  1               5                  10                  15

Asp Pro Ala Val Ser Arg Val Met Asn Met Lys Ile Glu Glu Thr Thr
             20                  25                  30

Met Thr Thr Gln Thr Pro Ala Pro Ile Gln Ala Pro Ser Ala Ile Leu
         35                  40                  45

Pro Leu Pro Gly Gln Ser Val Glu Arg Leu Cys Val Asp Pro Arg His
     50                  55                  60

Arg Gln Gly Pro Val Asn Leu Leu Ser Asp Pro Glu Gln Gly Val Glu
 65                  70                  75                  80

Val Thr Gly Gln Tyr Glu Arg Glu Lys Ala Gly Phe Ser Trp Ile Glu
                 85                  90                  95

Val Thr Phe Lys Asn Pro Leu Val Trp Val His Ala Ser Pro Glu His
            100                 105                 110

Val Val Val Thr Arg Asn Arg Arg Ser Ser Ala Tyr Lys Trp Lys Glu
        115                 120                 125

Thr Leu Phe Ser Val Met Pro Gly Leu Lys Met Thr Met Asp Lys Thr
    130                 135                 140

Gly Leu Leu Leu Leu Ser Asp Pro Asp Lys Val Thr Ile Gly Leu Leu
145                 150                 155                 160

Phe Trp Asp Gly Arg Gly Glu Gly Leu Arg Leu Leu Leu Arg Asp Thr
                165                 170                 175

Asp Arg Phe Ser Ser His Val Gly Gly Thr Leu Gly Gln Phe Tyr Gln
            180                 185                 190

Glu Val Leu Trp Gly Ser Pro Ala Ala Ser Asp Asp Gly Arg Arg Thr
        195                 200                 205

Leu Arg Val Gln Gly Asn Asp His Ser Ala Thr Arg Glu Arg Arg Leu
    210                 215                 220

Asp Tyr Gln Glu Gly Pro Pro Gly Val Glu Ile Ser Cys Trp Ser Val
225                 230                 235                 240

Glu Leu
```

<210> SEQ ID NO 15
<211> LENGTH: 726
<212> TYPE: DNA
<213> ORGANISM: Homo sapiens

<400> SEQUENCE: 15

```
cgtctggcca tcttgcctgc ttcagcacca ccagccacct caaatcctga tccagctgtg     60

tctcgtgtca tgaatatgaa aatcgaagaa acaaccatga caacccaaac cccagccccc    120

atacaggctc cctctgccat cctgccactg cctgggcaga gtgtggagcg gctctgtgtg    180

gaccccagac accgccaggg gccagtgaac ctgctctcag accctgagca aggggttgag    240
```

-continued

```
gtgactggcc agtatgagag ggagaaggct gggttctcat ggatcgaagt gaccttcaag    300

aaccccctgg tatgggttca cgcatcccct gaacacgtgg tggtgactcg gaaccgaaga    360

agctctgcgt acaagtggaa ggagacgcta ttctcagtga tgcccggcct gaagatgacc    420

atggacaaga cgggtctcct gctgctcagt gacccagaca aagtgaccat cggcctgttg    480

ttctgggatg gccgtgggga ggggctccgg ctccttctgc gtgacactga ccgcttctcc    540

agccacgttg gagggaccct tggccagttt taccaggagg tgctctgggg atctccagca    600

gcatcagatg acggcagacg cacgctgagg gttcagggca atgaccactc tgccaccaga    660

gagcgcaggc tggattacca ggaggggccc ccgggagtgg agatttcctg ctggtctgtg    720

gagctg                                                                726
```

```
<210> SEQ ID NO 16
<211> LENGTH: 1545
<212> TYPE: DNA
<213> ORGANISM: Artificial Sequence
<220> FEATURE:
<223> OTHER INFORMATION: Description of Artificial Sequence: Cloning DNA

<400> SEQUENCE: 16

gcggccgcgt cgacgcccgg cgcatccatg aggactcaga ctctgccctg cagctccagg     60

acttctacca ggaagtggcc aacccactgc tgacagcagt gaccttcgag tacccaagca    120

atgccgtgga ggaggtcact cagaacaact tccggctcct cttcaagggc tcagagatgg    180

tggtggctgg gaagctccag gaccgggggc ctgatgtgct cacagccaca gtcagtggga    240

agctgcctac acagaacatc actttccaaa cggagtccag tgtggcagag caggaggcgg    300

agttccagag ccccaagtat atcttccaca acttcatgga gaggctctgg gcatacctga    360

ctatccagca gctgctggag caaactgtct ccgcatccga tgctgatcag caggccctcc    420

ggaaccaagc gctgaattta tcacttgcct acagctttgt cacgcctctc acatctatgg    480

tagtcaccaa acccgatgac caagagcagt ctcaagttgc tgagaagccc atggaaggcg    540

aaagtagaaa caggaatgtc cactcagctg gagctgctgg ctcccggatg aatttcagac    600

ctggggttct cagctccagg caacttggac tcccaggacc tcctgatgtt cctgaccatg    660

ctgcttacca ccccttccgc cgtctggcca tcttgcctgc ttcagcacca ccagccacct    720

caaatcctga tccagctgtg tctcgtgtca tgaatatgaa aatcgaagaa acaaccatga    780

caacccaaac cccagccccc atacaggctc cctctgccat cctgccactg cctgggcaga    840

gtgtggagcg gctctgtgtg gaccccagac accgccaggg gccagtgaac ctgctctcag    900

accctgagca aggggttgag gtgactggcc agtatgagag ggagaaggct gggttctcat    960

ggatcgaagt gaccttcaag aaccccctgg tatgggttca cgcatcccct gaacacgtgg   1020

tggtgactcg gaaccgaaga agctctgcgt acaagtggaa ggagacgcta ttctcagtga   1080

tgcccggcct gaagatgacc atggacaaga cgggtctcct gctgctcagt gacccagaca   1140

aagtgaccat cggcctgttg ttctgggatg gccgtgggga ggggctccgg ctccttctgc   1200

gtgacactga ccgcttctcc agccacgttg gagggaccct tggccagttt taccaggagg   1260

tgctctgggg atctccagca gcatcagatg acggcagacg cacgctgagg gttcagggca   1320

atgaccactc tgccaccaga gagcgcaggc tggattacca ggaggggccc ccgggagtgg   1380

agatttcctg ctggtctgtg gagctgtagt tctgatggaa ggagctgtgc ccaccctgta   1440

cacttggctt ccccctgcaa ctgcagggcc gcttctgggg cctggaccac catggggagg   1500

aagagtccca ctcattacaa ataaagaaag gtggtgtgag cctga                   1545
```

-continued

<210> SEQ ID NO 17
<211> LENGTH: 921
<212> TYPE: PRT
<213> ORGANISM: hog

<400> SEQUENCE: 17

```
Met Lys Thr Leu Ser Pro Thr Gly Tyr Gly Leu Leu Leu Val Leu Pro
  1               5                  10                  15

Leu Leu Leu Ala Val Leu Gln Ser Thr Thr Ala His Lys Asn Asp Ile
             20                  25                  30

Asn Ile Tyr Ser Leu Thr Val Asp Ser Lys Val Ser Ser Arg Phe Ala
         35                  40                  45

His Thr Val Val Thr Ser Arg Val Val Asn Lys Gly Ser Ala Val Gln
     50                  55                  60

Glu Ala Thr Phe Gln Met Glu Leu Pro Lys Lys Ala Phe Ile Thr Asn
 65                  70                  75                  80

Phe Ser Met Ile Ile Asp Gly Val Thr Tyr Pro Gly Asn Ile Lys Glu
                 85                  90                  95

Lys Ala Ala Ala Gln Glu Gln Tyr Ser Ala Val Ala Arg Gly Glu Ser
            100                 105                 110

Ala Gly Leu Val Arg Ala Thr Gly Arg Lys Thr Glu Gln Phe Gln Val
        115                 120                 125

Ala Val Ser Val Ala Pro Ala Ala Lys Val Thr Phe Glu Leu Val Tyr
    130                 135                 140

Glu Glu Leu Leu Ala Arg His Leu Gly Val Tyr Glu Leu Leu Leu Lys
145                 150                 155                 160

Ile Gln Pro Gln Gln Leu Val Lys His Leu Gln Met Asp Ile His Ile
                165                 170                 175

Phe Glu Pro Gln Gly Ile Ser Phe Leu Glu Thr Glu Ser Thr Phe Met
            180                 185                 190

Thr Asn Glu Leu Ala Glu Ala Leu Thr Ile Ser Gln Asn Lys Thr Lys
        195                 200                 205

Ala His Ile Arg Phe Lys Pro Thr Leu Ser Gln Gln Gln Lys Ser Pro
    210                 215                 220

Glu Gln Gln Glu Thr Val Leu Asp Gly Asn Phe Ile Val Arg Tyr Asp
225                 230                 235                 240

Val Asn Arg Thr Val Thr Gly Gly Ser Ile Gln Ile Glu Asn Gly Tyr
                245                 250                 255

Phe Val His Tyr Phe Ala Pro Glu Val Trp Ser Ala Ile Pro Lys Asn
            260                 265                 270

Val Ile Phe Val Ile Asp Thr Ser Gly Ser Met Arg Gly Arg Lys Ile
        275                 280                 285

Gln Gln Thr Arg Glu Ala Leu Ile Lys Ile Leu Gly Asp Leu Gly Ser
    290                 295                 300

Arg Asp Gln Phe Asn Leu Val Ser Phe Ser Gly Glu Ala Pro Arg Arg
305                 310                 315                 320

Arg Ala Val Ala Ala Ser Ala Glu Asn Val Glu Glu Ala Lys Ser Tyr
                325                 330                 335

Ala Ala Glu Ile His Ala Gln Gly Gly Thr Asn Ile Asn Asp Ala Met
            340                 345                 350

Leu Met Ala Val Gln Leu Leu Glu Arg Ala Asn Arg Glu Glu Leu Leu
        355                 360                 365

Pro Ala Arg Ser Val Thr Phe Ile Ile Leu Leu Thr Asp Gly Asp Pro
```

-continued

```
    370                 375                 380

Thr Val Gly Glu Thr Asn Pro Ser Lys Ile Gln Lys Asn Val Arg Glu
385                 390                 395                 400

Ala Ile Asp Gly Gln His Ser Leu Phe Cys Leu Gly Phe Gly Phe Asp
                405                 410                 415

Val Pro Tyr Ala Phe Leu Glu Lys Met Ala Leu Glu Asn Gly Gly Leu
            420                 425                 430

Ala Arg Arg Ile Tyr Glu Asp Ser Asp Ser Ala Leu Gln Leu Glu Asp
        435                 440                 445

Phe Tyr Gln Glu Val Ala Asn Pro Leu Leu Arg Leu Val Ala Phe Glu
    450                 455                 460

Tyr Pro Ser Asn Ala Val Glu Glu Val Thr Gln Asp Asn Phe Arg Leu
465                 470                 475                 480

Phe Phe Lys Gly Ser Glu Leu Val Val Ala Gly Lys Leu Arg Asp Gln
                485                 490                 495

Ser Pro Asp Val Leu Ser Ala Lys Val Arg Gly Gln Leu His Met Glu
            500                 505                 510

Asn Val Thr Phe Val Met Glu Ser Arg Val Ala Glu Gln Glu Ala Glu
        515                 520                 525

Phe Leu Ser Pro Lys Tyr Ile Phe His Ser Phe Met Glu Arg Leu Trp
    530                 535                 540

Ala Tyr Leu Thr Ile Gln Gln Leu Leu Ala Gln Thr Val Ser Ala Ser
545                 550                 555                 560

Asp Ala Glu Lys Lys Ala Leu Glu Ala Arg Ala Leu Ser Leu Ser Leu
                565                 570                 575

Asn Tyr Ser Phe Val Thr Pro Leu Thr Ser Met Val Ile Thr Lys Pro
            580                 585                 590

Glu Gly Gln Glu Gln Ser Gln Val Ala Glu Lys Pro Val Glu Asn Gly
        595                 600                 605

Asn Arg Gln Gly Asn Thr His Ser Gly His Ser Ser Phe Gln Phe His
    610                 615                 620

Ser Val Gly Asp Arg Thr Ser Arg Leu Thr Gly Gly Ser Ser Val Asp
625                 630                 635                 640

Pro Val Phe Ser His Arg Arg Gly Trp Lys Gly Gln Ala Gln Gly Phe
                645                 650                 655

Glu Lys Met Ser Tyr Leu Pro Pro Arg Leu Gly Pro Pro Gly Pro Leu
            660                 665                 670

Gln Pro Thr Arg Phe Ser His Pro Phe Ser Arg Ile Thr Leu Asp Arg
        675                 680                 685

Val Leu Pro Glu Val Leu Ser Val Pro Asp Glu Thr Ser His Asp Met
    690                 695                 700

Asp Ser Arg Ile Ile Gly Ala Thr Ile Pro Pro Pro Pro Ala Arg Ile
705                 710                 715                 720

Gln Ala Pro Ser Val Ile Leu Pro Leu Pro Gly Gln Ser Val Asp Gln
                725                 730                 735

Leu Cys Val Asp Leu Lys His Ser Gln Gly Pro Val Lys Leu Leu Ser
            740                 745                 750

Asp Pro Gly Gln Gly Val Glu Val Thr Gly His Tyr Glu Arg Glu Lys
        755                 760                 765

Ala Arg Phe Ser Trp Ile Glu Val Thr Phe Lys His Pro Pro Leu Gln
    770                 775                 780

Val Arg Ala Ser Leu Glu His Ile Val Val Ile Arg Asn Arg Gln Ser
785                 790                 795                 800
```

-continued

```
Ser Ala Tyr Lys Trp Lys Glu Thr Leu Tyr Ser Val Met Pro Gly Leu
                805                 810                 815

Lys Ile Thr Met Asp Lys Ala Gly Leu Leu Leu Leu Ser Ser Pro Asn
            820                 825                 830

Arg Val Thr Ile Gly Leu Leu Ser Trp Asp Gly Pro Gly Lys Gly Leu
        835                 840                 845

Arg Leu Leu Leu Arg Asp Thr Asp His Phe Ser Ser Gln Ile Ser Gly
    850                 855                 860

Thr Phe Gly Gln Phe Tyr Gln Asp Val Val Trp Gly Pro Pro Ala Ala
865                 870                 875                 880

Ala Asp Asp Ser Lys Arg Thr Val Thr Val Gln Gly His Asp His Ser
                885                 890                 895

Ala Thr Arg Glu Leu Lys Leu Asp Tyr Gln Glu Gly Ser Pro Gly Lys
            900                 905                 910

Glu Ile Ser Cys Trp Thr Val Val Leu
        915                 920
```

<210> SEQ ID NO 18
<211> LENGTH: 2916
<212> TYPE: DNA
<213> ORGANISM: hog

<400> SEQUENCE: 18

```
gccaaaatga agaccctctc ccctactggc tacggccttc tgctggtcct gcccttgctg     60

ctggctgtcc ttcagagcac cacggcccac aagaatgaca tcaacatcta cagtctcacc    120

gtggactcca aggtctcgtc ccgatttgcc cacacagtcg ttaccagccg agtggtcaac    180

aagggcagtg ctgtgcagga ggccaccttc cagatggagc tgcccaagaa ggctttcatc    240

accaacttct ccatgatcat cgatggtgtg acctacccag gtaacatcaa ggagaaggct    300

gcagcccagg agcagtacag cgccgtggcc aggggagaga gtgctggcct tgtcagggcc    360

actgggagaa agacagagca gttccaggtg gcagtcagcg tggctcctgc tgccaaggtc    420

accttcgagc tggtgtatga ggagcttctg gcacggcatc tgggagttta tgagctgctg    480

ttgaaaatcc agccccagca gctggtcaag cacctgcaga tggacattca catcttcgag    540

cctcagggca tcagctttct ggagacagag agcaccttta tgaccaatga actggcagag    600

gccctcacca tatcacagaa caagactaag gctcacatcc gattcaagcc gacactctcc    660

cagcagcaga agtccccaga gcagcaggaa acagtcctgg atggcaactt catcgtccgc    720

tatgatgtga accggacagt cactgggggt tccattcaga tcgagaatgg ctactttgtg    780

cattactttg ccccggaggt ctggtctgca atacccaaga acgtgatctt tgtcattgac    840

acgagcggct ccatgagggg caggaaaatc cagcagaccc gggaagccct aattaagatc    900

ctgggtgacc tcggctcccg cgaccagttc aaccttgtca gcttcagtgg ggaagcaccc    960

aggagaaggg ctgttgcagc ctcagctgag aacgtggagg aagccaagag ctatgctgcc   1020

gaaatccatg cccagggagg gaccaatata aatgatgcga tgctgatggc cgtgcagctg   1080

ctggaaagag ccaaccggga ggagctgctg cccgcgagga gcgttacctt catcatcctc   1140

ctcaccgatg gcgaccctac tgtgggggag accaacccct cgaagatcca gaagaacgtt   1200

cgggaagcca tagacggcca gcacagcctc ttctgcctgg gcttcggctt tgacgtcccc   1260

tacgccttcc tggagaagat ggcactggag aatggcggtc tggcccggcg catctatgag   1320

gactctgact ctgccctgca gctcgaggac ttctaccagg aggtggccaa cccactgctg   1380
```

-continued

```
aggttggtgg cctttgagta cccaagcaat gccgtggagg aggtcacgca ggacaacttc   1440
cggctgttct tcaaaggctc tgagttggtg gtggccggga agctccggga ccagagcccc   1500
gatgtgctct ccgccaaagt caggggggcaa ctgcacatgg agaatgtcac cttcgtaatg   1560
gagtccaggg tagcagagca ggaggcggag ttcctgagcc ccaagtacat cttccacagc   1620
ttcatggaga gactctgggc atacctgacc atccagcaac tgttggcgca aacagtctct   1680
gcgtcagatg ctgagaagaa ggcccttgaa gcccgagccc tgagcttgtc actcaactac   1740
agctttgtca cccctctcac atctatggtg atcaccaaac ctgaaggcca agaacagtct   1800
caggttgctg agaagcccgt ggaaaatgga aaccgacagg ggaacaccca ctcaggtcac   1860
tcttcctttc aatttcattc tgtgggagac agaacatcca gactaacagg aggcagcagt   1920
gtagaccctg ttttttctca cagaagaggc tggaaaggac aagcccaagg ttttgagaaa   1980
atgtcctacc tcccaccgag attaggaccc cccggacctc ttcagcctac tcgtttttct   2040
catccgtttt cccgtataac cttggaccgg gtgctgccag aggtgctatc cgttcctgat   2100
gaaacgtcac atgacatgga ttcaagaatc ataggagcca cgatacctcc accccctgcc   2160
cgcatccagg ctccttccgt catcttgcca ctgcctgggc agagcgtgga ccagctctgt   2220
gtggacctca agcactccca gggcccagtg aagctgctct cagaccctgg ccaaggggtt   2280
gaagtgactg gccactatga gagggagaag gcccgcttct catggattga agtgaccttc   2340
aagcacccgc cactgcaggt tcgtgcatcc ctggagcaca tagtagtgat tcggaaccgc   2400
caaagctctg cgtacaagtg gaaggaaaca ctctactcag tgatgcccgg cctcaagata   2460
accatggaca aggcgggact tcttctgctc agcagcccaa acagagtgac catcggcctg   2520
ctgtcctggg atggccctgg gaaggggctc cgactccttc tgcgggacac tgaccacttc   2580
tccagccaga tcagtgggac ctttggccag ttttaccagg acgtggtctg ggaccccca    2640
gcagcagcag atgacagcaa gcgaacagtg acagtccagg gacatgacca ctctgccacc   2700
agagagctca agctggatta ccaagaggga tccccgggaa aagagatttc ctgctggact   2760
gtggtgctgt agttctgatg ggaggagtta cacccgcccc ccatgctgcc ccctttttgc   2820
agatggctgc cacactgtaa cacaggtcag cctgtgggcc ctggaacatc atggggagat   2880
gtattttcac tcattaaaat aaagagaggt gatgtg                             2916

<210> SEQ ID NO 19
<211> LENGTH: 227
<212> TYPE: PRT
<213> ORGANISM: hog

<400> SEQUENCE: 19

Ser Val Pro Asp Glu Thr Ser His Asp Met Asp Ser Arg Ile Ile Gly
1               5                   10                  15

Ala Thr Ile Pro Pro Pro Pro Ala Arg Ile Gln Ala Pro Ala Pro Ile
            20                  25                  30

Leu Pro Leu Pro Gly Gln Ser Val Asp Gln Leu Cys Val Asp Leu Lys
        35                  40                  45

His Ser Gln Gly Pro Val Lys Leu Leu Ser Asp Pro Gly Gln Gly Val
    50                  55                  60

Glu Val Thr Gly His Tyr Glu Arg Glu Lys Ala Arg Phe Ser Trp Ile
65                  70                  75                  80

Glu Val Thr Phe Lys His Pro Pro Leu Gln Val Arg Ala Ser Leu Glu
                85                  90                  95

His Ile Val Val Ile Arg Asn Arg Gln Ser Ser Ala Tyr Lys Trp Lys
```

-continued

```
            100                 105                 110

Glu Thr Leu Tyr Ser Val Met Pro Gly Leu Lys Ile Thr Met Asp Lys
        115                 120                 125

Ala Gly Leu Leu Leu Leu Ser Ser Pro Asn Arg Val Thr Ile Gly Leu
    130                 135                 140

Leu Ser Trp Asp Gly Pro Gly Lys Gly Leu Arg Leu Leu Leu Arg Asp
145                 150                 155                 160

Thr Asp His Phe Ser Ser Gln Ile Ser Gly Thr Phe Gly Gln Phe Tyr
                165                 170                 175

Gln Asp Val Val Trp Gly Pro Pro Ala Ala Ala Asp Asp Ser Lys Arg
            180                 185                 190

Thr Val Thr Val Gln Gly His Asp His Ser Ala Thr Arg Glu Leu Lys
        195                 200                 205

Leu Asp Tyr Gln Glu Gly Ser Pro Gly Lys Glu Ile Ser Cys Trp Thr
    210                 215                 220

Val Val Leu
225


<210> SEQ ID NO 20
<211> LENGTH: 681
<212> TYPE: DNA
<213> ORGANISM: hog

<400> SEQUENCE: 20

tccgttcctg atgaaacgtc acatgacatg gattcaagaa tcataggagc cacgatacct      60

ccaccccctg cccgcatcca ggctccttcc gtcatcttgc cactgcctgg gcagagcgtg     120

gaccagctct gtgtggacct caagcactcc cagggcccag tgaagctgct ctcagaccct     180

ggccaagggg ttgaagtgac tggccactat gagagggaga aggcccgctt ctcatggatt     240

gaagtgacct tcaagcaccc gccactgcag gttcgtgcat ccctggagca catagtagtg     300

attcggaacc gccaaagctc tgcgtacaag tggaaggaaa cactctactc agtgatgccc     360

ggcctcaaga taaccatgga caaggcggga cttcttctgc tcagcagccc aaacagagtg     420

accatcggcc tgctgtcctg ggatggccct gggaaggggc tccgactcct tctgcgggac     480

actgaccact tctccagcca gatcagtggg acctttggcc agttttacca ggacgtggtc     540

tggggacccc cagcagcagc agatgacagc aagcgaacag tgacagtcca gggacatgac     600

cactctgcca ccagagagct caagctggat taccaagagg gatccccggg aaaagagatt     660

tcctgctgga ctgtggtgct g                                               681


<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:PCR primer

<400> SEQUENCE: 21

cgggatccgt gctagacctg ccatccttat cctc                                  34


<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 22
```

-continued ccgctcgagg tatcttcacc gtccagcagg aaatctct 38

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence:PCR primer

<400> SEQUENCE: 23
cgggatcccg aactggagac aaatgaagag ccctg 35

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence:PCR primer

<400> SEQUENCE: 24
cggaattccg tttgcttccc cactgaacac aatgatattg a 41

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence:PCR primer

<400> SEQUENCE: 25
cgggatccct gtgctctttg tcattgataa aagcgg 36

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence:PCR primer

<400> SEQUENCE: 26
cggaattccc tgcctgccgt agtcaatgct agaa 34

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence:PCR primer

<400> SEQUENCE: 27
cgggatcccg catttcaaga ctcctaccac aggatctaa 39

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence:PCR primer

<400> SEQUENCE: 28
cggaattcct atcttcaccg tccagcagga aatctct 37

<210> SEQ ID NO 29
<211> LENGTH: 32
<212> TYPE: DNA

-continued

```
<213> ORGANISM: Artificial Sequence
<220> FEATURE:
<223> OTHER INFORMATION: Description of Artificial Sequence:PCR primer

<400> SEQUENCE: 29

cgggatcccg tctggccatc ttgcctgctt ca                                32


<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence:PCR primer

<400> SEQUENCE: 30

ccgctcgagg cagctccaca gaccagcagg aaatct                            36
```

PROTEIN INDUCED BY HOMOGENEOUS BLOOD TRANSFUSION AND DNA ENCODING THE SAME

TECHNICAL FIELD

The present invention relates to a protein having immunosuppressive activity, to a gene encoding the protein, to a vector containing the gene, to a transformant produced by the vector, to a method of manufacturing a protein having immunosuppressive activity by culturing the transformant, to a medicinal composition containing the protein and the like.

BACKGROUND ART

Organ transplantation is a technique which has already been established as a final treatment for end-stage organ failure. From a medical standpoint, the greatest problem for organ transplantation is acute and chronic organ rejection. Clinically effective drugs which are currently in use include such powerful immunosuppressants as adrenocortical hormone, cyclosporin, tacrolimus, azathioprine, anti-thymocyte antibodies and the like. However, these drugs have a general depressant effect on the host's immune system. Such immunosuppression is usually a factor in the main causes of death following organ transplantation, including organ rejection, infection and malignant tumors. Therefore, it would seem that in addition to antigen-specific immunosuppression, safer and more successful transplantation could be achieved if immune tolerance was artificially introduced, making it possible for the organ to survive permanently with only initial treatment.

Moreover, the aforementioned immunosuppressants are also seen as promising prophylactic or therapeutic agents for auto-immune disorders such as rheumatism and psoriasis and allergic disorders such as allergic asthma (bronchial asthma and the like), allergic rhinitis, allergic conjunctivitis, allergic dermatitis (atopic dermatitis and the like) and pollinosis, or antirejection drug.

It has long been known that renal transplants are more successful in renal failure patients who receive repeated preoperative blood transfusions (Opelz G et al, *Lancet* 1, 696–698 (1974)). It has also been recognized that a more effective immune reaction is induced by allogeneic blood transfusion in which the transfusion is specifically matched to the donor (donor specific blood transfusion) (Opelz G et al, *Transplant Proc* 17, 2357–2361 (1985)) and verified by many experimental tests. In experiments with rodents, complete immune tolerance was induced in many cases through a single allogeneic blood transfusion (Marino H et al, *Am J Surg* 95, 267–273 (1958); Marquet et al, *Transplant Proc III,* 708–710 (1971); Fabre J W et al, *Transplantation* 14, 608–616 (1972)).

There have also been a variety of reports on the mechanism by which allogeneic blood transfusion might induce immune tolerance. Generally speaking, the mechanisms are depending on either cellular or humoral factors (Kobayashi, Eiji, *Molecular Medicine* 34, 796–804 (1997)). Clonal delation (Cranston D et al, *Transplantation* 42, 302–306 (1986)) and anergy (Dollman M J et al, *J Exp Med* 173, 79–87 (1991)) belong in the former mechanism, while the latter mechanism includes bioactive substances in vivo induced by allogeneic blood transfusion which are biologically active in vivo. One of humoral factors is anti-idiotype antibody, which has been shown to be produced immediately after allogeneic blood transfusion in animals (NagarkattI P S et al, *Transplantation* 36, 695–699 (1983); Downey W E III et al, *Transplantation* 49, 160–166 (1990); Baldwon W M III et al, *Transplantation,* 51, 481–485 (1991)) and humans (Horuzxko A et al, *Immunology Letters* 26, 127–130 (1990)), but less is known about the others.

And since bioactive substances derived through allogeneic transfusion which exhibit immunosuppression are endogenous substances, they can be expected to have fewer side effects than existing immunosuppressants.

DISCLOSURE OF THE INVENTION

Using an allogeneic blood transfusion model to resolve the aforementioned problems, the inventors discovered a novel protein produced in the blood which has immunosuppressive activity and perfected the present invention.

The present invention provides the following proteins and the like.

Item 1. A protein (a) or (b) below:

(a) a protein comprising the amino acid sequence shown by SEQ ID NO:14;

(b) a protein comprising the amino acid sequence as defined in (a) wherein one or more amino acids are deleted, replaced or added and having immunosuppressive activity.

Item 2. A protein (a) or (b) below:

(a) a protein having the amino acid sequence shown by SEQ ID NO:1;

(b) a protein comprising the amino acid sequence as defined in (a) wherein one or more amino acids are deleted, replaced or added and having immunosuppressive activity.

Item 3. A protein (a) or (b) below:

(a) a protein comprising the amino acid sequence shown by SEQ ID NO:8;

(b) a protein comprising the amino acid sequence as defined in (a) wherein one or more amino acids are deleted, replaced or and added and having immunosuppressive activity.

Item 4. A gene encoding the protein as defined in any one of Items 1 through 3.

Item 5. A gene comprising a DNA (a) or (b) below:

(a) a DNA comprising the nucleotide sequence shown by SEQ ID NO:15;

(b) a DNA which hybridizes under stringent conditions with a DNA comprising the nucleotide sequence as defined in (a), and which encodes a protein having immunosuppressive activity.

Item 6. A gene comprising a DNA (a) or (b) below:

(a) a DNA comprising the nucleotide sequence shown by SEQ ID NO:2;

(b) a DNA which hybridizes under stringent conditions with a DNA comprising the nucleotide sequence as defined in (a), and which encodes a protein having immunosuppressive activity.

Item 7. A gene comprising a DNA (a) or (b) below:

(a) a DNA comprising the nucleotide sequence shown by SEQ ID NO:9;

(b) a DNA which hybridizes under stringent conditions with DNA comprising the nucleotide sequence as defined in (a), and which encodes a protein having immunosuppressive activity.

Item 8. A protein having an amino acid sequence encoded by the gene as defined in any one of Items 4 through 7.

Item 9. A vector containing the gene as defined in any one of Items 4 through 7.

Item 10. A transformant containing the vector as defined in Item 9.

Item 11. A method of manufacturing a protein comprising:

Step 1 of culturing the transformant as described in Item 10; and

Step 2 of collecting a protein having immunosuppressive activity from the culture obtained in the said step.

Item 12. A medicinal composition containing any one of the protein defined in any one of Items 1 through 3 or Item 8 as an active ingredient, together with a pharmacologically acceptable carrier.

Item 13. The medicinal composition as defined in Item 12, wherein the medicinal composition is an immunosuppressant.

Item 14. The medicinal composition as defined in Item 13, wherein the immunosuppressant is a prophylactic or therapeutic agent for an auto-immune disorder or allergic disorder, or an antirejection drug.

Item 15. The medicinal composition as defined in Item 14, wherein the auto-immune disorder is rheumatism or psoriasis.

Item 16. The medicinal composition as defined in Item 14, wherein the allergic disorder is bronchial asthma, allergic rhinitis, allergic dermatitis or pollinosis.

Representation of amino acids, peptides, nucleotide sequences, nucleic acids and the like by abbreviations in this description is in conformity with the rules recommended by the IUPAC-IUB, "*Guidelines for Writing Descriptions Containing Nucleotide sequences or Amino Acid Sequences*" (edited by Japanese Patent Office), and the conventions relating to use of codes or symbols in the art.

Moreover, in the present invention "gene" ("DNA") includes not only double-stranded DNA but also single-stranded DNA comprising a sense or anti-sense strand thereof, and there are no limits on its length. Therefore, unless otherwise specified, the gene (DNA) of the present invention includes double-stranded DNA including human genome DNA, single-stranded DNA (sense strand) including cDNA, single-stranded DNA (anti-sense strand) having a sequence complementary to the sense strand, and fragments thereof.

The protein having immunosuppressive activity of the present invention can be obtained for example by the following method. When transfusing 1 ml of the heparinized whole blood of 8–10 week-old DA rats (allogeneic blood transfusion) into the veins or portal veins, preferably the portal veins, of 8–10 week-old Lewis rats, and isolating and purifying from the tissue, cells or blood of the Lewis rats after 4–28 days or preferably one week, extract obtained by homogenizing the animals' tissue or cells and then extracting with acid and the like, or preferably whole blood obtained from the abdominal aorta is collected and centrifuged at 0–20° C., preferably 4° C., and collecting a serum fraction containing the protein of the present invention.

The protein of the present invention can be purified and isolated from the extract or preferably the serum containing the protein of the present invention obtained by the aforementioned methods by a combination of such purification methods as salting out, dialysis, gel filtration, reversed phase chromatography, ion exchange chromatography, affinity chromatography and other forms of chromatography.

The immunosuppressive activity of the protein of the present invention can be assayed using a variety of immune reactions employing mouse, rat or human lymphocytes, for example immunosuppressive activity can be assayed with high sensitivity by adding the immunosuppressive substance in an allogeneic mixed lymphocyte reaction (MLR) of mice, rats or humans. A substance which exhibits immunosuppressive activity in allogeneic MLR is promising candidates for immunosuppression. They are particularly useful as drugs for auto-immune disorders such as rheumatism and psoriasis as well as allergic disorders such as allergic asthma (bronchial asthma and the like), allergic rhinitis, allergic conjunctivitis, allergic dermatitis (atopic dermatitis and the like) and pollinosis, and antirejection drugs.

A 26 kDa protein having immunosuppressive activity (hereinafter referred to below as "MAY-I") which was newly isolated and identified by the present inventors was broken into suitable fragments, and the amino acid sequences of the fragments were determined and compared to known amino acid sequences. As a result, the presence of fragments having amino acid sequences matching amino acids 699–725, 785–789 or 897–900 of the amino acid sequence of inter-alpha-inhibitor H4P heavy chain-rat (GeneBank accessions No. Y11283: hereinafter referred to hereunder as rat IαIH4P) (SEQ ID No. 6) was confirmed. The amino acid sequences matching amino acids 699–725, 785–789 or 897–900 of rat IαIH4P are given as SEQ ID NO:3, 4 and 5, respectively.

The expected molecular weight of the protein from amino acid 699 of rat IαIH4P to the C-terminal amino acid was 26 kDa, the same as that of MAY-I. The inventors then cloned the cDNA sequence (SEQ ID NO:2) of MAY-I in a polymerase chain reaction (PCR) from the cDNA sequence of rat IαIH4P. This cDNA sequence of MAY-I was then transferred into a protein expression vector, preparing recombinant MAY-I. This recombinant MAY-I exhibited immunosuppressive activity when subjected to allogeneic MLR. Consequently, it was shown that in terms of its structure MAY-I is identical to a protein having the amino acid sequence of rat IαIH4P from amino acid 699 to the C-terminal.

In addition, the inventors cloned the entire cDNA sequence (SEQ ID NO:9) of rat IαIH4P, prepared a recombinant protein having the amino acids of SEQ ID NO:8, and performed allogeneic MLR to confirm immunosuppressive activity. They then removed the sequence (SEQ ID NO:2) corresponding to MAY-I from the cDNA sequence of SEQ ID NO:9, prepared a recombinant protein having an amino acid sequence excluding the amino acid sequence corresponding to MAY-I, and performed allogeneic MLR to confirm that it did not exhibit immunosuppressive activity, thus showing that it is MAY-I that controls the immunosuppressive function.

Proteins resembling rat IαIH4P also exists in humans, including human PK-120 and human IHRP, and these proteins as a class are known as IαIH4P (Hitoshi N et al, *FEBS Lett* 357, 207–211 (1995) (PK-120), Carl H H et al, U.S. Pat. No. 5,459,063 (1989) (sgp120), Ken H et al, *J Biochem* 119, 577–584 (1996) (IHRP)). The amino acid sequence and DNA sequence of human PK-120 are shown by SEQ ID NO:12 and 13, respectively, while the amino acid sequence and DNA sequence of human IHRP are shown by SEQ ID NO:10and 11, respectively. Despite some differences in their amino acid sequences and DNA sequences, human PK-120 and human IHRP exhibit extremely high homology (homology analysis of GeneBank sequence database accession No. D38595 (human IHRP) and GeneBank sequence database accessions No. D38535 (human PK-120)). Moreover, it is clear that the amino acid sequence of human IHRP (SEQ ID NO:10) and the amino acid sequence of rat IαIH4P (SEQ ID NO:6) are also highly homologous (Souey E et al, *Biochem Biophys Res Commun* 243, 522–530 (1998)). The cDNA sequences of the two also exhibit 73% homology (homology analysis of rat IαIH4P nucleotide sequence (SEQ ID NO:7), GeneBank nucleotide sequence database accessions No. Y11283, and human IHRP nucleotide sequence (SEQ ID NO:11), GeneBank nucleotide sequence accessions No. D38595), suggesting that this protein is preserved across species. We then cloned the cDNA sequence (SEQ ID NO:15) encoding the amino acid sequence (SEQ ID NO:14) corresponding to MAY-I in the human IHRP amino acid sequence (SEQ ID NO:10), and combined it with a protein expression vector to prepare recombinant human MAY-I. When subjected to allogeneic MLR, this recombinant MAY-I exhibited immunosuppressive activity. This suggests that the amino acid sequence (SEQ ID NO:10) of human IHRP which contains the amino acid sequence of (SEQ ID NO:14), and the amino acid sequence (SEQ ID NO:12) of human PK-120, which is highly homologous to the amino acid sequence of human IHRP, may have immunosuppressive activity in humans similar to that of human MAY-I. It is also conceivable that other IαIH4P proteins may also produce immunosuppression in humans if they contain an amino acid sequence identical to that of MAY-I or an amino acid sequence which has been modified only to the extent that the immunosuppressive activity of MAY-I is not lost.

Since the nucleotide sequence of pig IαIH4P (SEQ ID NO:18) (Ken H et al, *J Biochem* 119, 577–584 (1996)) is also highly homologous with the DNA sequence of rat IαIH4P, it is likely that as in the case of human IαIH4P, a protein comprising the amino acid sequence of pig IαIH4P (SEQ ID NO:17) or the amino acid sequence (SEQ ID NO:19) corresponding to MAY-I therein would have immunosuppressive activity in humans. A nucleotide sequence encoding for an amino acid sequence corresponding to the MAY-I segment of the amino acid sequence of pig IαIH4P is shown as SEQ ID NO:20.

Moreover, an amino acid sequence corresponding to MAY-I in the amino acid sequences of the IαIH4P of other mammals might also have the same immunosuppressive activity as pig IαIH4P. The present invention encompasses (a) a protein comprising an amino acid sequence corresponding to MAY-I in the amino acid sequences of the IαIH4P of mammals other than rats, humans and pigs, or (b) a protein comprising an amino acid sequence (a) with one or more amino acids deleted, replaced or added and having immunosuppressive activity. In addition, the present invention encompasses gene encoding aforementioned amino acid sequences in (a) or (b).

The protein of the present invention has an immunosuppressive effect. The amino acid sequence expressed by SEQ ID NO:14 is an amino acid sequence which was induced based on the nucleotide sequence of a gene which was cloned in an Example of this Description. The protein of the present invention is a protein comprising the amino acid sequence expressed by SEQ ID NO:14. The present invention also encompasses a protein comprising this amino acid sequence with one or more amino acids deleted, replaced or added and having immunosuppressive activity. In the present Description, "more" in "one or more" signifies 2–50 or preferably 2–30 or more preferably 2–20 or ideally 2 to a few.

Moreover, a protein of the present invention is a protein comprising the amino acid sequence expressed by SEQ ID NO:1. The present invention also encompasses a protein comprising this amino acid sequence with one or more amino acids deleted, replaced or added and having immunosuppressive activity.

Moreover, a protein of the present invention is a protein comprising the amino acid sequence expressed by SEQ ID NO:8. The present invention also encompasses a protein comprising this amino acid sequence with one or more amino acids deleted, replaced or added and having immunosuppressive activity.

The present invention also encompasses a protein having immunosuppressive activity which comprises amino acids having 70% or greater, preferably 80% or greater or more preferably 95% or greater homology with the amino acid sequences of any of (SEQ ID NO:14, 1 or 8. Moreover, a gene encoding said proteins is also included in the present invention.

In general, naturally-occurring proteins may be subject to deletion, addition, replacement and other changes to radicals in the amino acid sequence due to polymorphisms or mutations in the gene encoding therefor or to modifications after protein formation, but nonetheless retain the same physiological activity as the unmutated protein. It is also possible to artificially create genetic mutations using the techniques of gene recombination, in such a way that the physiological activity of the protein is effectively unchanged. A protein comprising the amino acid sequence of SEQ ID NO:1, 8 or 14 which has been altered by such a natural or artificial mutation is also included in the proteins of the present invention as long as it retains the immunosuppressive function, and naturally or artificially mutated gene is included in the gene of the present invention as long as the protein comprising the amino acid sequence encoded by said gene retains its immunosuppressive action. Alleles of these are also included.

Methods of creating the artificial mutations include genetic engineering techniques such as site specific mutagenesis (*Methods in Enzymology* 154:350 & 367–382, 1987 and 100:468, 1983; *Nucleic Acids Res* 12:9441, 1984; *A Course in Successive Chemical Experimentation I, "Genetic Research II"*, Nihon Seikagakukai p 105, 1986), techniques of chemical synthesis such as the phosphotriester and phosphoamidite methods (*J Am Chem Soc* 89:4801, 1967 and 91:3350, 1969; *Science* 150:178, 1968; *Tetrahedron Lett* 22:1859, 1981 and 24:245, 1983), and combinations of these methods. Specifically, DNA synthesis may be by chemical synthesis using the phosphoamidite method or phosphotriester method, and may be performed on a commercially available automated oligonucleotide synthesizer. Double-strand fragments may be obtained from the chemically synthesized single-strand product by either synthesizing a complementary strand and annealing the strands together under appropriate conditions, or by adding the complementary strand using DNA polymerase together with an appropriate primer sequence.

There are no particular limitations on the origin of the protein of the present invention, which may be a natural protein, a recombinant protein or a chemically synthesized protein. When a natural protein is desired, a culture of tissue or cultured cells expressing the target protein may be used as the starting material, and purification accomplished by a suitable combination of well-known methods of protein purification such as salting out, affinity chromatography, ion exchange chromatography, gel filtration and the like. For example, when affinity chromatography is used the target protein can be purified using a carrier to which have been bound antibodies against the protein of the present invention.

When a recombinant protein is desired, a recombinant expression vector obtained by cloning DNA of the present invention which encodes the aforementioned target protein in a suitable expression vector is transferred to a host (*E. coli*, yeast etc.), and the transformant cultured under suitable conditions to produce the target protein. For purposes of isolating the target protein, it is generally desirable that the target protein by secreted into the culture supernatant, which can be achieved by optionally selecting the combination of recombination vector and host and culture conditions. Manufacture of a protein comprising the desired amino acid sequence by chemical synthesis can also be done optionally by the person skilled in the art.

Suitable pharmacologically acceptable modifications can also be added to the protein of the present invention as long as its immunosuppressive activity is maintained. That is, although the proteins comprising the amino acid sequences shown by SEQ ID NO:14, 1 and 8 or comprising a partial amino acid sequence shown thereby normally have a carboxyl (—COOH) or carboxylate (—COO—) group at the C-terminal, the C-terminal may also be an amide (—$CONH_2$) or ester (—COOR). The R of the ester may be for example $C_{1-6}$ alkyl group such as a methyl, ethyl, n-propyl, isopropyl, n-butyl, $C_{3-8}$ cycloalkyl group such as a cyclopentyl, cyclohexyl, $C_{6-12}$ aryl group such as a phenyl, α-naphthyl, $C_{7-14}$ aralkyl group such as phenyl-$C_{1-2}$ alkyl (e.g., a benzyl, phenethyl, benzhydryl and the like), α-naphthyl-$C_{1-2}$ alkyl (e.g., an α-naphthylmethyl and the like), or pivaloyloxymethyl ester, which is a widely used ester for oral use. Possible salts of the protein of the present invention include pharmacologically acceptable bases (such as alkali metals) and acid salts (organic and inorganic acids), pharmacologically acceptable acid-added salts are particularly desirable. Examples of such salts include salts of inorganic acids (such as hydrochloric acid, phosphoric acid, hydrobromic acid and sulfuric acid) and salts of organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid). The protein of the present invention and precursors, amides and esters thereof have immunosuppressive activity and are useful as drugs and in particular as prophylactic and therapeutic agent for autoimmune disorders (rheumatism, psoriasis and the like) or allergic disorders (allergic asthma (bronchial asthma), allergic rhinitis, allergic conjunctivitis, allergic dermatitis (atopic dermatitis), pollinosis and the like), and antirejection drug.

The gene of the present invention encodes a protein having immunosuppressive activity. Specifically, the gene of the present invention is DNA which encodes a protein having the amino acid sequence of either SEQ ID NO:14, 1 or 8, or one of these with one or more amino acids deleted, replaced or added, and having immunosuppressive activity. Moreover, the gene of the present invention contains a DNA which comprises the nucleotide sequence of either SEQ ID NO:15, 2 or 9, or which hybridizes under stringent conditions with DNA with such a nucleotide sequence, and encodes a protein having immunosuppressive activity. The gene of the present invention can also be used in gene therapy.

There are no particular limits on the stringent hybridization conditions, although in general, conditions are selected so that the probe DNA sequence and the DNA sequence to be detected are as homologous as possible. Stringent hybridization conditions can be achieved by adjusting the solvent concentration and/or salt concentration of the hybridization solution, the hybridization temperature, the hybridization time and the like. The washing conditions after hybridization (salt concentration of the washing liquid and the like) can also be adjusted. Such conditions can be suitably selected by the person skilled in the art depending on the length and/or base composition of the probe, and the degree of homology between the nucleotide sequence to be detected and the nucleotide sequence of the probe.

The gene of the present invention can also be manufactured by the following genetic engineering methods. Methods of cloning the gene of the present invention including using a synthetic DNA primer having a partial nucleotide sequence of the protein of the present invention to amplify the target DNA from genome DNA, genome DNA library or the tissues, cells or preferably liver of humans or warm-blooded animals by known PCR methods, or selecting DNA incorporated into a suitable vector by hybridization with labeled DNA with synthetic DNA or DNA fragments having a part or all of the regions of the protein of the present invention. Methods of hybridization include for example those described in *Molecular Cloning* (2nd Ed., J Sambrook et al, Cold Spring Harbor Lab Press, 1989). When using a commercial library, the methods described in the attached manual may be employed. The cloned DNA encoding the protein of the present invention can be used either as is or if desired may be digested with a restriction enzyme or have a linker added. Said DNA may have ATG as the translation start codon at the 5' terminal, or TAA, TGA or TAG as the translation stop codon at the 3' terminal. These start and stop codons may also be added using a suitable synthetic DNA adapter.

A vector containing the gene of the present invention is provided by the present invention. There are no particular limits on the type of vector, which can be selected according to the purpose for which it will be used. In general it is possible to use plasmid vectors and phage vectors, which are available commercially. An expression vector is used in order to produce the recombinant proteins encoded by the gene of the present invention.

The expression vector for the protein of the present invention can be manufactured for example by (a) cutting the target DNA fragment from the DNA encoding for the protein of the present invention, and (b) attaching said DNA fragment downstream the promoter in a suitable expression vector. Vectors which may be used include plasmids derived from *E. coli* (such as pBR322, pBR325, pUC12 and pUC13), plasmids derived from *Bacillus subtilis* (such as pUB110, pTP5 and pC194), plasmids derived from yeasts (such as pSH19 and pSH15), bacteriophages such as λ phage, retroviruses, Vaccinia virus, Baculoviridae and other animal viruses. The promoter used in the present invention may be any promoter suited to the host used to express the DNA.

A transformant produced by transferring a recombinant vector into a host is provided by the present invention. Any suitable living creature can be used as the host, such as for example eucaryotic microorganisms (animals cells, plant cells, yeasts and the like) and prokaryotic microorganisms (*E. coli* and the like). Methods known by the person skilled in the art can be used for transformation, including specifically the calcium phosphate, electroporation, microinjection and lipofection methods and the like.

When the host for transformation consists of animal cells, a SV40-derived promoter, retrovirus promoter, metallothionein promoter, heat shock promoter, cytomegalovirus promoter or SRα promoter or the like may be used. When the host is an *Escherichia*, a trp promoter, T7 promoter, lac promoter, recA promoter, λPL promoter, 1pp promoter or the like is desirable, while if it is a *Bacillus*, an SPO1 promoter, SPO2 promoter, penP promoter or the like is desirable, and if the host is a yeast, a PHO5 promoter, PGK promoter, GAP promoter, ADH1 promoter or GAL promoter or the like is preferred. When the host consists of insect cells, a polyhedrin promoter or P10 promoter or the like is desirable. In addition, the expression vector may contain enhancers, splicing signals, PolyA addition signals, selection markers and SV40 replication origins (sometimes abbreviated herein as SV40ori). Possible selection markers include for example the dihydrofolic acid reductase (sometimes abbreviated herein as dhfr) gene (methotrexate (MTX) resistant), ampicillin resistance gene (sometimes abbreviated herein as Ampr) and neomycin resistance gene (G418 resistant, sometimes abbreviated herein as Neo). In particular, when using CHO ($dhfr^-$) cells and the DHFR gene as the selection marker, selection can also be accomplished with a medium that does not contain thymidine. If necessary, a signal sequence matched to the host can also be added to the N-terminal of the protein or partial peptide thereof. A phoA signal sequence, OmpA signal sequence or the like can be used if the host is an *Escherichia,* an α-amylase signal sequence, subtilisin signal sequence or the like if the host is a *Bacillus,* a mating factor α (MFα) signal sequence, invertase signal sequence or the like if the host is a yeast, and an insulin signal sequence, α-interferon signal sequence, antibody molecule signal sequence or the like if the host is animals cells. The transformant can be manufactured using a vector containing DNA constructed as noted above encoding for the protein.

Possible hosts include for example *Escherichia, Bacillus,* yeasts, insects, insect cells, animal cells and the like. Of the *Escherichia, Escherichia coli* K12 DH1 (*Proc Natl Acad Sci USA* 60, 160, 1968), JM103 (*Nucleic Acids Research* 9, 309, 1981), JA221 (*Journal of Molecular Biology* 120, 517, 1978), HB101 (*Journal of Molecular Biology* 41, 459, 1969), C600 (*Genetics* 39, 440, 1954) or the like can be used. Of the *Bacillus, Bacillus subtilis* MI114 (*Gene* 24, 255, 1983) or 207–21 (*Journal of Biochemistry* 95, 87, 1984) or the like can be used.

Yeasts such as *Saccaromyces cerevisiae* AH22, $AH22R^-$, NA87-11A, DKD-5D and 20B-12 can be used. Possible insects include for example bombic larvae (Maeda et al., *Nature,* Vol. 315, 592 (1985)). In terms of insect cells, for example if the virus is AcNPV, established cell lines derived from *Spodoptera frugiperda* larvae (Sf cells), MG1 cells from the mid-intestines of *Trichoplusia ni,* High Five TM cells from *Trichoplusia ni* eggs, or cells derived from *Mamestra brassicae, Estigmena acrea* or the like may be used. If the virus is BmNPV, an established *Bombyx mori* N cell line (BmN cells) or the like may be used. Sf cells that may be used include for example Sf9 cells (ATCC CRL1711) and Sf21 cells (both from Vaughn, J L, In Vitro 13, 213–217, 1977). Animal cells which may be used include for example monkey COS-7 cells, Vero cells, CHO chinese hamster cells, CHO chinese hamster cells lacking the DHFR gene (dhfr-CHO cells), mouse L cells, mouse 3T3 cells, mouse myeloma cells, human HEK293 cells, human FL cells, 293 cells, C127 cells, BALB 3T3 cells, Sp-2/O cells and the like. Transformation of *Escherichia* can be accomplished for example by the methods described in *Proc Natl Acad Sci USA* 69, 2110, 1972 or *Gene* 17, 107, 1982 or the like. Transformation of *Bacillus* can be accomplished for example by the methods described in *Molecular & General Genetics* 168, 111, 1979. Transformation of yeasts can be accomplished for example by the methods described in *Proc Natl Acad Sci USA* 75, 1929, 1978.

Transformation of insect cells or insects can be accomplished for example by the methods described in *Bio/Technology* 6, 47–55, 1988. Transformation of animal cells can be accomplished for example by the methods described in *Virology* 52, 456, 1973. Introduction of the expression vector into the cells can be accomplished for example by the lipofection method (Felgner, P L et al, *Proceedings of the National Academy of Sciences of the United States of America* 84, 7413, 1987), the calcium phosphate method (Graham, F L and van der Eb, A J, *Virology* 52, 456–467, 1973) or the electroporation method (Neumann E et al, *EMBO J.* 1, 841–845, 1982) or the like. A transformant transformed by an expression vector containing DNA encoding the protein of the present invention is obtained in this way. Methods of stably expressing the protein, etc. of the present invention using animal cells include methods of selecting by clone selection those cells in which the expression vector introduced into the cells has been incorporated into the chromosomes. Specifically, transformants are selected using the aforementioned selection marker as the reference. Moreover, a stable animal cell strain with high expression of the protein, etc. of the present invention can be obtained by repeated clone selection of animal cells obtained in this way using a selection marker. When the dhfr gene is used as the selection marker, DNA encoding the protein, partial peptide thereof or the like of the present invention can be amplified in the cells together with the dhfr gene by gradually increasing the MTX concentration of the culture and selecting for resistance strain, to obtain an animal cell strain with even higher expression. The protein or the like of the present invention can then be manufactured by culturing the transformant in conditions under which DNA encoding the protein or the like of the present invention can be expressed, and producing and accumulating the protein or the like of the present invention.

There are no particular limitations on the medicinal composition of the present invention as long as it contains the protein of the present invention. The medicinal composition of the present invention may also contain physiologically allowable carriers, excipients and the like as usage in addition to the protein of the present invention.

The immunosuppressant of the present invention is useful as a prophylactic or therapy for auto-immune disorders (rheumatism, psoriasis and the like) or allergic disorders (allergic asthma (bronchial asthma), allergic rhinitis, allergic conjunctivitis, allergic dermatitis (atopic dermatitis), pollinosis and the like), and antirejection drugs.

Conventional methods can be employed when the protein or DNA encoding therefor of the present invention is used as the aforementioned medicinal composition. For example, if necessary it may be administered orally in the form of a sugar-coated or enteric-coated tablet, capsule, elixir, microcapsules or the like, externally as an ointment, plaster or the like, nasally as a spray, inhalant or the like, or parenterally by injecting a suspension or sterile solution made with water or other pharmacologically acceptable liquid. Possible methods of administering the protein of the present invention for treatment of organ transplant rejection include oral administration, injection, intraarticular administration, intrarectal administration, perfusion for the transplanted organ, administration to the transplanted organ and administration through a balloon catheter. It can be manufactured for example by formulating the compound or salt thereof together with physiologically acceptable carriers, flavorings, excipients, vehicles, preservatives, stabilizers, binders and the like in the dosage form required by generally accepted pharmaceutical practice. The amount of active component in such formulations is designed to provide a dose within the indicated range. The best modes of administration are injection, inhalation, nasal drops, external administration and other forms of topical administration.

Additives which may be blended into tablets and capsules include for example binders such as gelatin, corn starch, gum tragacanth and gum arabic, excipients such as crystal cellulose, swellings such as corn starch, gelatin and alginic acid, lubricants such as magnesium stearate, sweeteners such as sucrose, lactose or saccharin, and flavorings such as peppermint, akamono oil and cherry. A capsule formulation may also contain oils and other liquid carriers in addition to the previous types of ingredients. Sterile compositions for purposes of injection may be formulated by ordinary methods such as dissolving or suspending active ingredients, sesame oil, coconut oil and other naturally vegetable oils in a vehicle such as injectable water. Aqueous injections include for example physiological saline and isotonic solutions containing glucose and other adjuvants (such as D-sorbitol, D-mannitol, sodium chloride and the like), and suitable solubilizers such as alcohols (i.e. ethanol), polyalcohols (i.e. propylene glycol, polyethylene glycol) and nonionic surfactants (i.e. polysorbate 80 (TM), HCO-50) may also be added. Oily liquids such as sesame oil and soy bean oil may also be added, as can solubilizers such as benzyl benzoate and benzyl alcohol. Buffers (such as phosphate buffers and sodium acetate buffers), analgesics (such as benzalconium chloride and procaine hydrochloride), stabilizers (such as human serum albumin and polyethylene glycol), preservatives (such as benzyl alcohol and phenol) and antioxidants may also be used. The prepared injection is normally used to fill ampoles. Since the resulting formulation is stable and of low toxicity, it can be administered for example to humans and other mammals (such as mice, rats, guinea pigs, rabbits, chickens, sheep, pigs, cows, cats, dogs, monkeys, sacred baboons, chimpanzees and the like).

The dosage per day of the protein of the present invention or DNA encoding therefor varies depending on symptoms and the like, but in the case of oral administration it is normally between about 0.0001 g and 10 g or preferably about 0.1 mg and 100 mg or more preferably about 1.0 mg and 50 mg or ideally about 1.0 mg and 20 mg per day for an adult transplant patient (weight 60 kg). In the case of parenteral administration, the single dosage varies depending on the patient, organ, symptoms and method of administration. For example when the protein of the present invention or DNA coding therefor is injected to an adult transplant patient (weight 60 kg), an intravenous injection at a dosage between about 0.00001 g and 1 g or preferably about 0.01 mg and 30 mg or more preferably about 0.1 mg and 20 mg or ideally about 0.1 mg and 10 mg per day is desirable. The dosage is applicable to other animals.

BEST MODE FOR CARRYING OUT THE INVENTION

Figure 1:
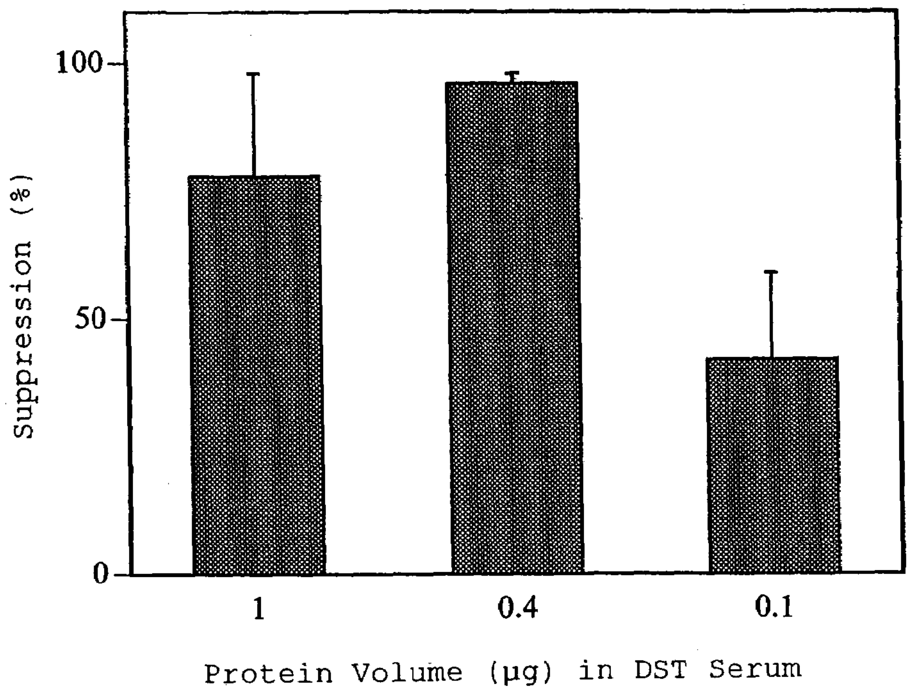
FIG. 1 shows the immunosuppressive activity of allogeneic transfusion serum in allogeneic rat MLR.

The present invention is explained in more detail below with reference to examples, but is not limited by these examples.

EXAMPLE 1

Immunosuppressive Activity Induced by Allogeneic Blood Transfusion 1 ml of the heparinized whole blood of 8–10 week-old DA rats was transfused into the portal veins of 8–10 week-old Lewis rats (allogeneic transfusion), and one week later all blood was collected from the abdominal aortas of the Lewis rats. As a control, 1 ml of the heparinized whole blood of Lewis rats was also transfused into the portal veins of Lewis rats (blood transfusion: abbreviated hereunder as "BT"), and one week later all blood was collected from the abdominal aortas of the Lewis rats. The blood of the subject rats and that of control rats was centrifuged at 4° C., and the serum fraction collected (referred to hereunder as allogeneic transfusion serum and BT serum respectively). Protein concentrations in the allogeneic transfusion and BT serum were measured, concentrations of 1, 0.4 and 0.1 μg were added to allogeneic rat MLR, and the immunosuppressive activity was compared. Protein concentrations in the serums were measured using a commercial BCA protein assay kit (Pierce) in accordance with the enclosed directions. In the allogeneic MLR, Lewis rat spleen cells were used as the reaction cells and DA rat mitomycin C-treated (or irradiated) spleen cells as the stimulus cells, and the two cultured together in equal amounts.

The reaction cells were prepared as follows. Spleens were removed from 8–10 week-old Lewis rats, and lymphocytes were prepared by specific gravity centrifugation using Lympholyte®-Rat (Cedarlane). The lymphocytes were adjusted to $10^6$/ml using an RPMI-1640 medium (Nikken Biomedical Laboratory, containing penicillin 100 units/ml, streptomycin 100 μg/ml, N-2-hydroxyethylpiperazine-N'-2-ethanesulfonate 10 mM, 2-mercaptoethanol 55 μM) supplemented with 10% heat inactivated fetal bovine serum (hereunder "FBS"), and used as the reaction cell suspension wherein the reaction cells floated. The stimulus cells were prepared as follows. Spleen cells were removed from 8–10 week-old DA rats, and lymphocytes prepared by specific gravity centrifugation using Lympholyte®-Rat. The lymphocytes were suspended in RPMI-1640 medium supplemented with 10% FBS, and treated with 25 μg/ml mytomycin C at 37° C. for 15 minutes. After washed three times, they were adjusted to $10^6$/ml using RPMI-1640 containing 10% FBS, and used as the stimulus cell suspension wherein the stimulus cells floated. 100 μl of the reaction cell suspension and 100 μl of the stimulus cell suspension prepared as described above, together with 2 μl of the specimen, were added to 96-hole U-bottom microtest plate, and cultured for 3 days at 37° C. under the condition of 5% carbon dioxide and 95% air. Blastogenesis of lymphocytes in allogeneic rat MLR was measured using $^3$H-thymidine incorporation as the marker. That is, 1 μuCi/well of $^3$H-thymidine was added 18 hours before completion of the culture, and after completion of culture cells were collected in a cell harvester, and radioactivity in the cells was measured with a microplate scintillation counter and used as a marker of allogeneic MLR lymphocyte blastogenesis. The suppressive activity of the allogeneic rat MLR was evaluated by calculating the suppression rate according to the formula below.

Suppression rate (%)={1−(cpm of MLR with specimen added−cpm of reaction cells only)/(cpm of MLR without specimen−cpm of reaction cells only)}×100.

The results show that allogeneic transfusion serum exhibits obvious immunosuppressive activity at a protein mass of 0.4 μg (FIG. 1).

EXAMPLE 2

Isolation and Purification of a Bioactive Substance (Protein) which Suppresses Allogeneic Rat MLR The allogeneic transfusion serum obtained in Example 1 was isolated and purified by the following methods.

1. Salting out

The allogeneic transfusion serum was salted out with 40% ammonium sulfate and the precipitate dissolved in 20 mM sodium phosphate buffer (pH 7.0), and the solution was dialyzed. This solution was centrifuged at 4° C., and the supernatant collected.

2. Protein G affinity column chromatography

Figure 2:
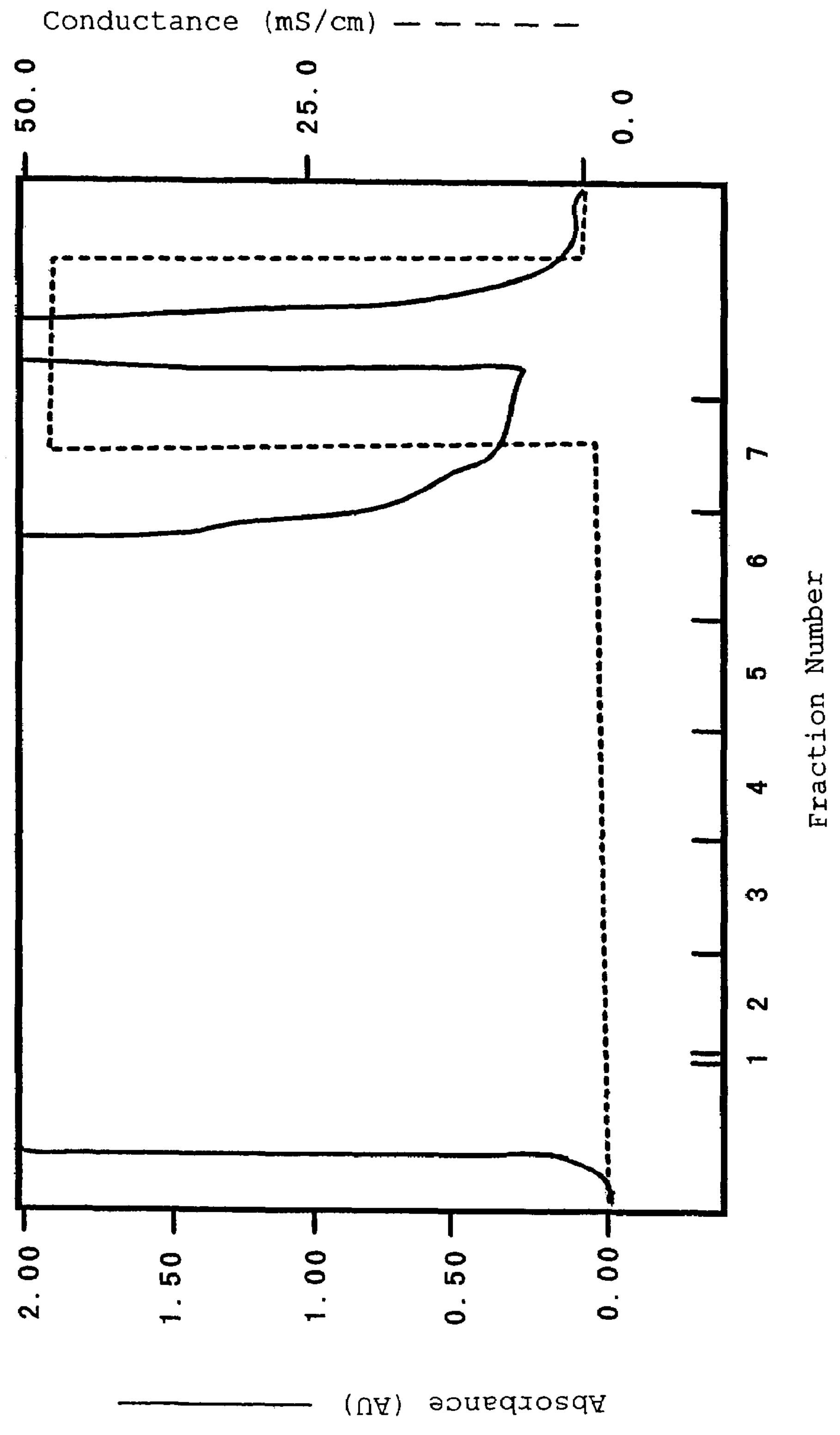
FIG. 2 shows a chromatogram of allogeneic transfusion serum by protein G affinity column.
Figure 3:
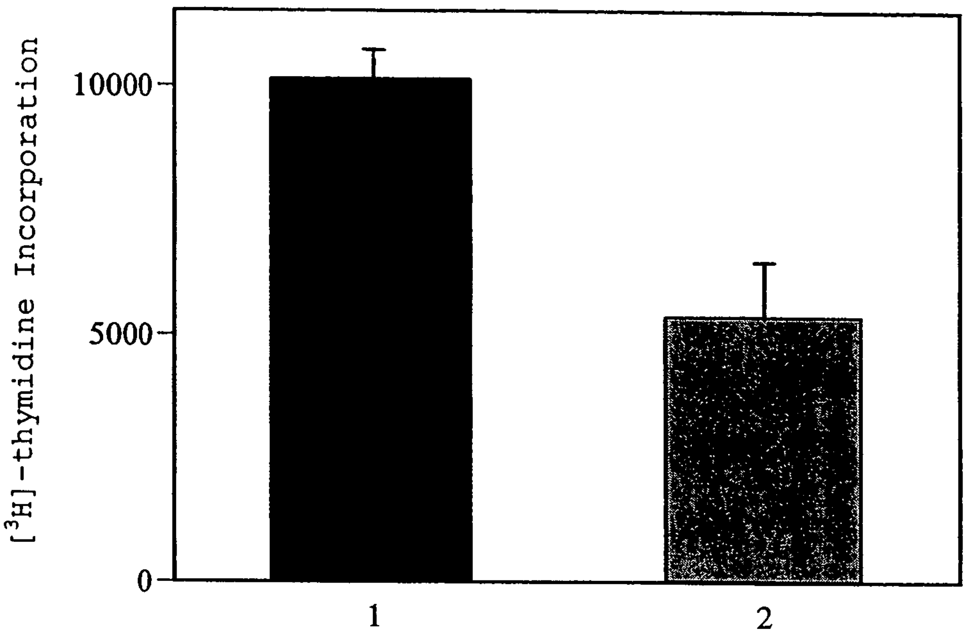
FIG. 3 shows the immunosuppressive activity in allogeneic rat MLR of the fraction that did not bind to the protein G affinity column.

The salted-out sample was isolated and purified by medium-pressure chromatography using a Protein G column (Pharmacia) (FIG. 2). Isolation was performed with a binding solution of 50 mM potassium phosphate buffer (pH 7.0), an eluant of 100 mM glycine-hydrochloric acid solution (pH 2.7) and a flow rate of 200 μl/minute. The resulting proteins No. 2–7 (described hereunder as "Protein G flow through" or "PGFT") including proteins that did not bind to the column exhibited clear immunosuppressive activity in allogeneic rat MLR (FIG. 3).

3. Hydroxyapatite chromatography

Figure 4:
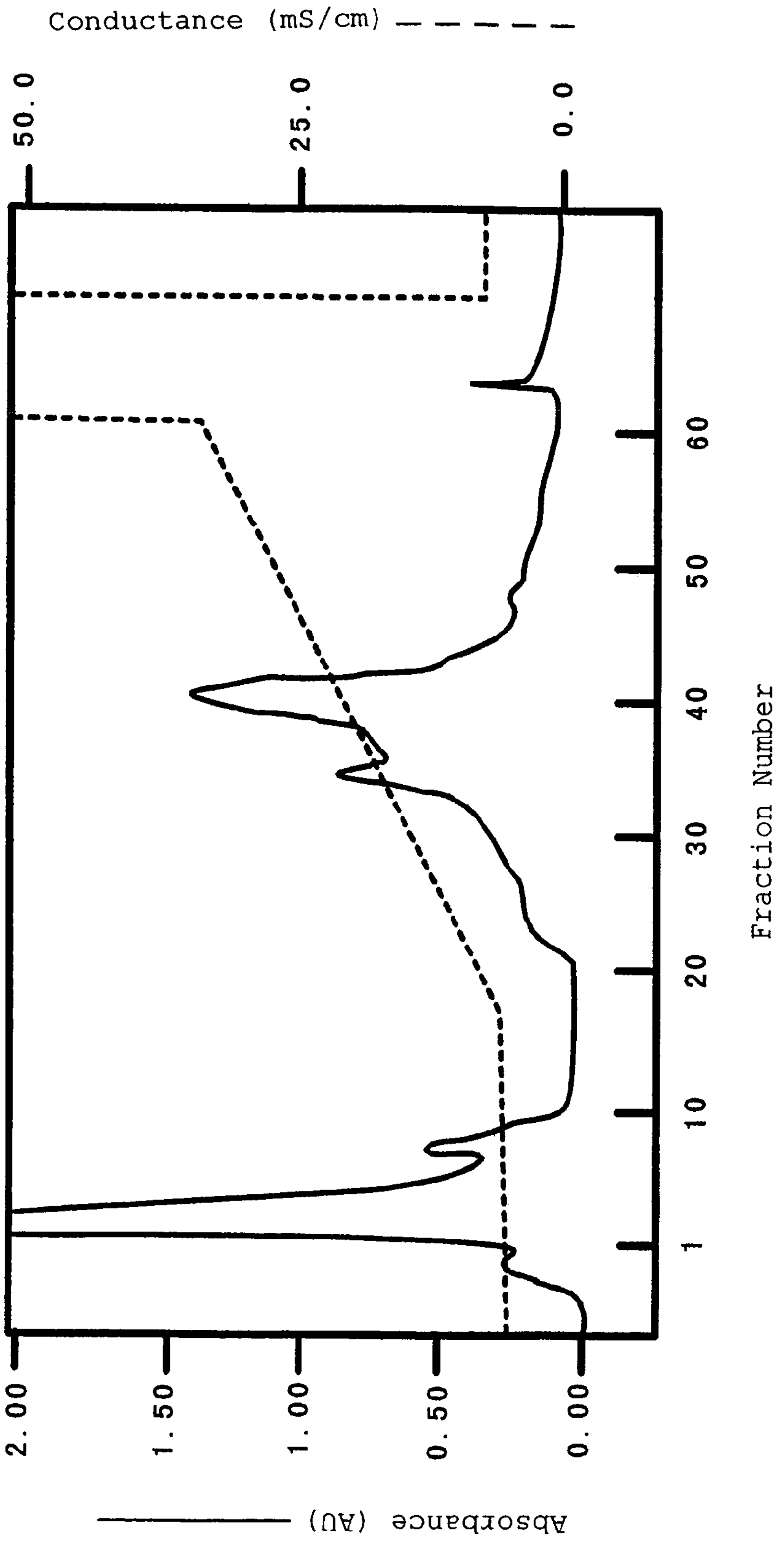
FIG. 4 shows a hydroxyapatite chromatograph of the fraction that did not bind to the protein G affinity column.
Figure 5:
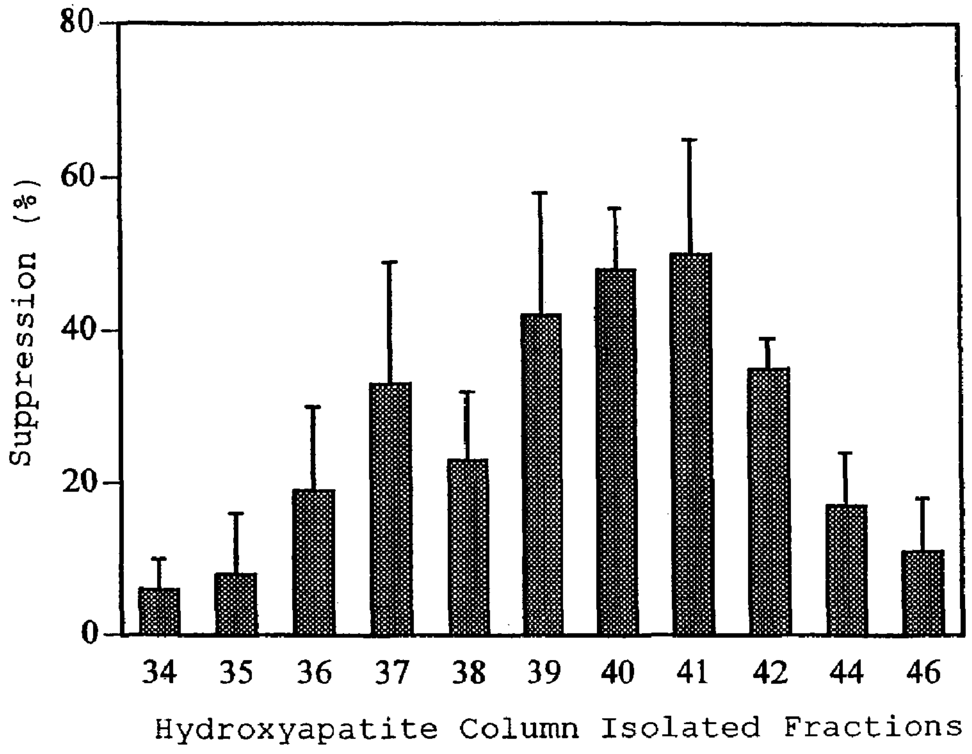
FIG. 5 shows the immunosuppressive activity in allogeneic rat MLR of the fraction isolated by hydroxyapatite chromatography.

The PGFT was isolated and purified by medium-pressure chromatography using a CHT20 (Bio-Rad) column (FIG. 4). Isolation was performed with a binding solution of 50 mM potassium phosphate buffer (pH 6.8), an eluant of 500 mM potassium phosphate buffer (pH 6.8), a gradient capacity of 300 ml and a flow rate of 2 ml/minute. When the immunosuppressive activity of the resulting isolated fractions was investigated by allogeneic rat MLR, Fractions No. 39–42 exhibited immunosuppressive activity (referred to hereunder as "CHT 39-42", FIG. 5).

4. Gel filtration chromatography

Figure 6:
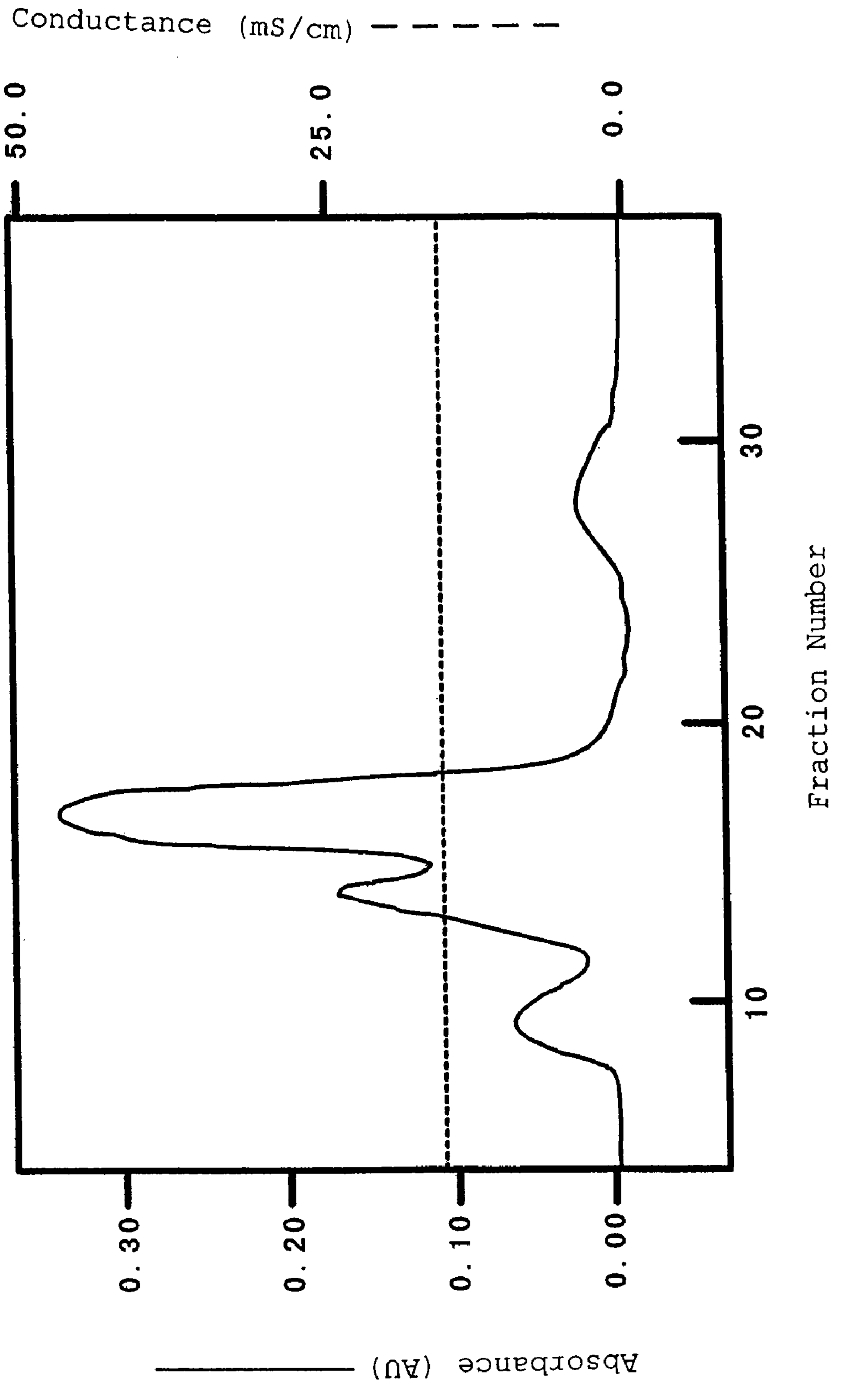
FIG. 6 shows a gel filtration chromatogram of the fraction recognized by hydroxyapatite chromatography as having immunosuppressive activity.
Figure 7:
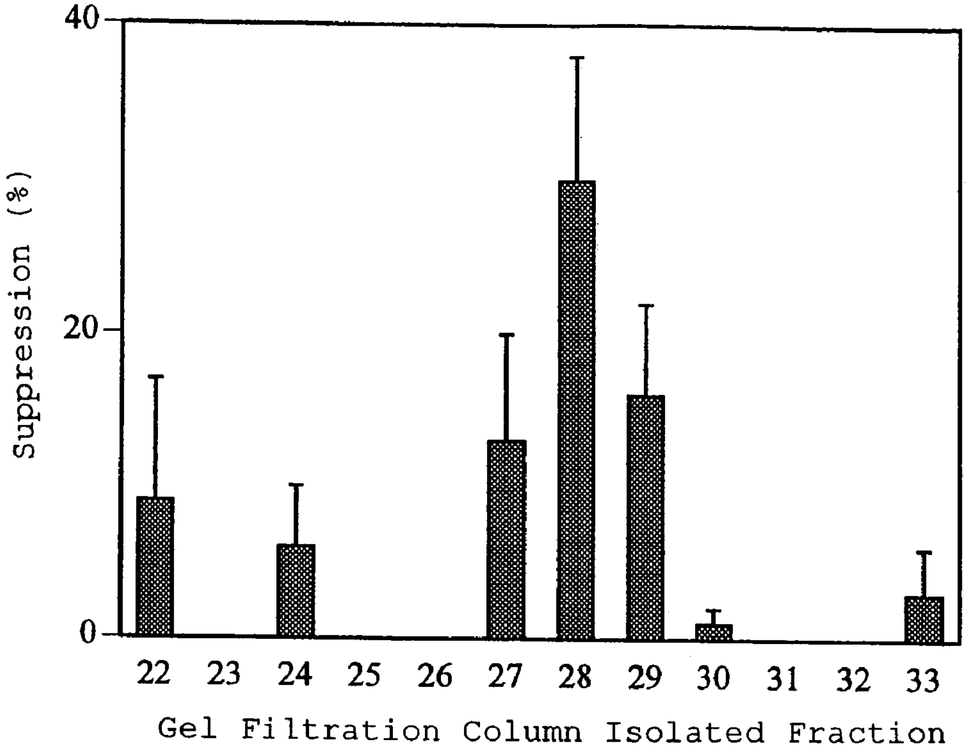
FIG. 7 shows the immunosuppressive activity in allogeneic rat MLR of the fraction isolated by gel filtration chromatography.

CHT 39-42 were isolated and purified by medium-pressure chromatography using a HiLoad Superdex 200 pg (Pharmacia) (FIG. 6). Isolation was performed with 20 mM sodium phosphate buffer/150 mM sodium chloride (pH 7.4), at a flow rate of 0.8 ml/minute. When the immunosuppressive activity of the isolated fractions was investigated by allogeneic rat MLR, Fractions No. 28 and 29 (described below as "SD28" and "SD29") exhibited immunosuppressive activity (FIG. 7).

EXAMPLE 3

Figure 8:
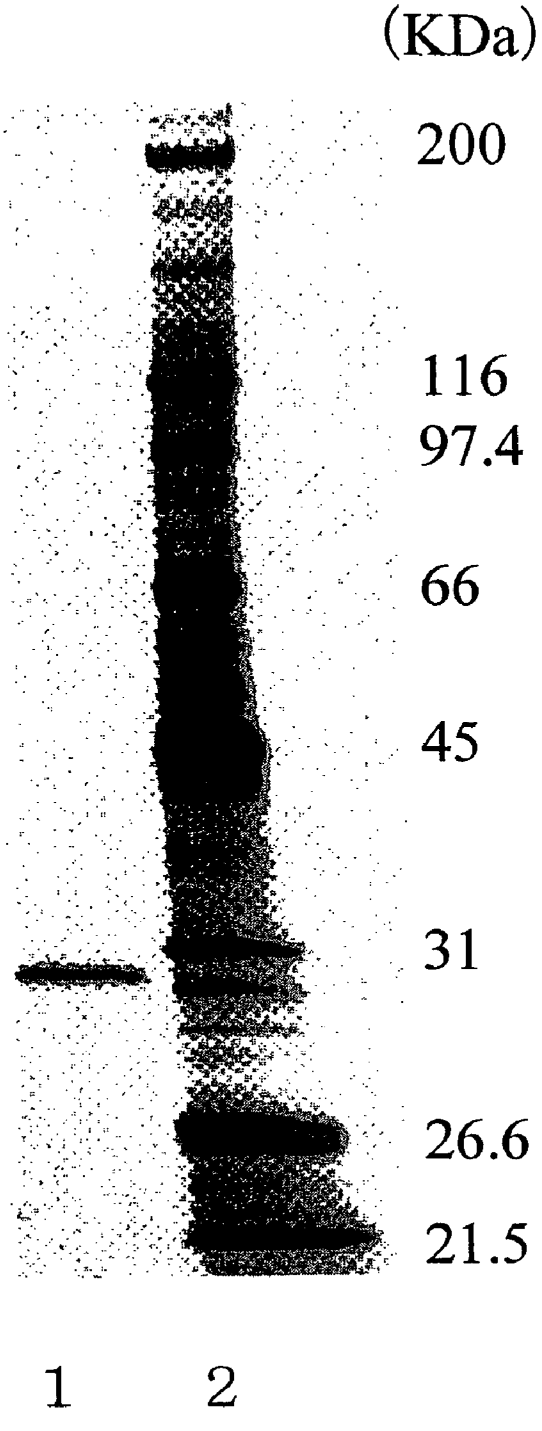
FIG. 8 is an SDS-polyacrylamide gel electrophoresis photograph of the Fr. 28 isolated by gel filtration chromatography, showing that it is a single protein.

Confirmation by SDS-PAGE of Purity of Bioactive Substance (Protein) which Suppresses Allogeneic Rat MLR The purity of the protein in the purification process was evaluated by SDS-polacrylamide gel electrophoresis (SDS-PAGE). SDS-PAGE was performed according to the methods described in *Protein Test Notes* (*Part* 2)—*Through Determination of Primary Structure* (Yodosha), pp. 14–19, and following electrophoresis the gel was stained according to the silver stain method described on p. 22 of the above. The results of SDS-PAGE showed that SD 28 and 29 were one type of protein (protein contained in SD28 is referred to below as MAY-I, FIG. 8).

The purity of the MAY-I having immunosuppressive activity obtained by these purification and isolation methods reached about 1.5×10$^8$ times (Table 1).

TABLE 1

| Purification stage | Content (ml) | Protein volume (mg) | Purity |
|---|---|---|---|
| Serum | 182 | 14924000 | 1.0 |
| Salting out | 80 | 816000 | 18.3 |
| Protein G | 78 | 476580 | 31.3 |
| CHT20 | 20 | 15120 | 987.0 |
| Superdex 200 pg | 20 | 0.098 | 152909836.1 |

EXAMPLE 4

Analysis of N-terminal and Internal Partial Amino Acid Sequence of a Protein (MAY-I) which Suppresses Allogeneic Rat MLR The amino acid sequence of the protein (MAY-I) purified in Example 2 which is contained in SD28 and 29 and has immunosuppressive activity was determined. The N-terminal amino acid sequence of the protein was analyzed by a protein sequencer (G1005A Protein Sequencing System, Hewlett-Packard) according to the phenyl isothiocyanate method. The internal partial amino acid sequence of the protein was analyzed by breaking the protein's disulfide bonds by carboxymethylization, fragmenting it with lysyl endopeptidase, isolating the peptides with reverse-phase HPLC and analyzing them with the aforementioned protein sequencer. The same amino acid sequence (27 amino acids from the N-terminal, (SEQ ID NO:3) was obtained from both fractions. The amino acid sequences shown by SEQ ID NO:4 and 5 were also found inside the protein.

EXAMPLE 5

Analysis of Molecular Weight of Bioactive Substance (MAY-I) which Suppresses Allogeneic Rat MLR The molecular weight of MAY-I was measured by ion spray mass analysis using a mass spectrometer (API3000, Perkin Elmer Sciex). The results show a protein with a molecular weight of 26089.84 Da.

EXAMPLE 6

Identification of a Gene Fragment Encoding Rat IαIH4P

The 27 N-terminal amino acids (SEQ ID NO:3) analyzed in Example 4 were subjected to a homology search on the protein database recorded on the GenomeNet FASTA Server (Kyoto Center). The results showed perfect homology with amino acids number 699–725 of the amino acid sequence of rat IαIH4P, recorded as accession number JC5953. The amino acid sequences shown as (SEQ ID NO:4 and 5 were shown to be completely homologous with amino acids 785–789 and 897–900, respectively, of the amino acid sequence of rat IαIH4P.

Moreover, the anticipated molecular weight of the protein from amino acid 699 to the C-terminal amino acid of rat IαIH4P, which was shown to be homologous with the 27 amino acids of (SEQ ID No. 3, was calculated to be 26080.07 Da, or effectively identical to the molecular weight of the protein (MAY-I) shown in Example 5. Consequently, this protein encodes the sequence beginning with amino acid 699 of rat IαIH4P.

EXAMPLE 7

Cloning of DNA Encoding the Sequence (MAY-I) Beginning with Amino Acid 699 of the Amino Acid Sequence of the Rat IαIH4P Obtained in Example 6

The part corresponding to the amino acids from 699 through the C-terminal was cloned by PCR from the total cDNA sequence of rat IαIH4P as recorded in the GeneBank database under accessions number Y11283. Namely, 1 ml of the heparinized whole blood of 9 week-old DA rats was tranfused (allogeneic transfusion) into the portal veins of 9 week-old Lewis rats, the livers of which were removed one week later and used to prepare total RNA using Isogen (Nippon Gene) according to the manual. cDNA was synthesized with M-MLV reverse transcriptase (GIBCO BRL) from the resulting 10 μg of total RNA using a 6-base random primer (TAKARA). PCR was performed with the resulting 1 μg of cDNA as the template. The nucleotide sequences shown by SEQ ID Nos. 21 and 22 were prepared as the PCR primers. The PCR reaction was performed with an Advantage 2 PCR Kit (Clontech) using 2 μl of each primer, 1 μl of AdvanTaq DNA polymerase, the reaction buffer included with the enzymes, dNTPs and 1 μl of the cDNA, with a total capacity of 40 μl. After the template DNA was thoroughly denatured through 1 minute of heat treatment at 94° C., a cycle of 1 minute at 94° C., 1 minute at 62° C. and 1 minute at 68° C. was repeated 25 times, followed by the elongation reaction for 3 minutes at 68° C. After completion of the reaction, 1.2% agarose gel electrophoresis was performed using 10 μl of the reaction liquid and the amplification product detected with an ethidium bromide stain. A roughly 700 bp band was then removed with a razor blade, centrifugally filtered (UltraFree, Millipore), phenol extracted and ethanol precipitated, and a DNA fragment collected. This DNA fragment was digested with restriction enzymes BamH I and Xho I, subcloned to the BamH I and Xho I sites of protein expression vector psec Tag2 B (Invitrogen), and introduced into *E. coli* DH5α to obtain *E. coli* DH5α/MAY I-pSec Tag2 B. A sequencing reaction was performed on the nucleotide sequence of the cDNA fragment inserted into the resulting transformant with an ABI PRISM DyeTerminator Cycle Sequencing Ready Reaction Kit (Perkin Elmer Applied Biosystems) sequencing reaction, using a T7 primer and a pcDNA 3.1/BGH reverse primer. Analysis of this cDNA sequence with an ABI PRISM 377 DNA Sequencer produced a cDNA sequence (SEQ ID NO:2) encoding for the protein (MAY-1) between amino acid 699 of rat IαIH4P and the C-terminal amino acid.

EXAMPLE 8

Cloning the Total cDNA Nucleotide Sequence of Rat IαIH4P

PCR was performed using 1 μg of the rat liver cDNA synthesized in Example 7 as the template. The nucleotide sequences shown by SEQ ID Nos. 23, 24, 25, 26, 27 and 28 were synthesized as the PCR primers. The PCR reaction was performed by the same methods as in Example 7. Following agarose gel electrophoresis, the DNA fragment (H4P-1) amplified by SEQ ID NO:23 and 24, the DNA fragment amplified by SEQ ID NO:25 and 26 (H4P-2) and the DNA fragment amplified by SEQ ID NO:27 and 28 (H4P-3) were collected from the gel, digested with restriction enzymes BamH I and EcoR I, subcloned to the BamH I and EcoR I sites of protein expression vector pEF4/Myc-His C (Invitrogen), and introduced into *E. coli* SCS110 (Stratagene) to obtain *E. coli* SCS110/H4P-1, 2 & 3. After confirmation of the nucleotide sequence of the inserted cDNA, the plasmid vectors containing fragments H4P-1 and H4P-2 were digested with restriction enzymes BamH I, EcoR I and Bgl II, subcloned again into pEF4/Myc-His C and introduced into *E. coli* SCS110 to obtain *E. coli* SCS110/partial-H4P which did not include cDNA encoding for the MAY-I protein. After confirmation of the nucleotide sequence of the resulting partial-H4P cDNA, it was digested together with H4P-3 using restriction enzymes BamH I, EcoR I and Xba I, subcloned again into pEF4/Myc-His C, and introduced into *E. coli* DH5α to obtain *E. coli* DH5α/H4P containing the total cDNA nucleotide sequence of rat IαIH4P.

EXAMPLE 9

Preparation of the Protein (MAY-I) Corresponding to the Amino Acid Sequence Between 699 and the C-terminal Amino Acid of the Rat IαIH4P Obtained in Example 7, and Preparation of the Complete Rat IαIH4P Protein (H4P) and the Protein (Partial-H4P) Excluding the cDNA Encoding the Amino Acid Sequence of MAY-I Obtained in Example 8

The MAY-I-pSec Tag2 B prepared in Example 7 and the H4P and partial-H4P prepared in Example 8 were transfectioned to COS 7 cells by the DEAE-Dextran method. The day after transfection, they were transferred to an FBS-free medium and cultured for 24 hours, after which the culture supernatant was collected and the recombinant MAY-I, H4P and partial-H4P therein isolated and purified by the following methods. Namely, the culture supernatant was isolated and purified by medium-pressure chromatography using an His-Trap column (Amersham-Pharmacia). Isolation was performed with a 20 mM sodium phosphate buffer-10 mM imidazole solution (pH 7.4) as the binding solution and a 20 mM sodium phosphate buffer-500 mM imidazole solution (pH 7.4) as the eluant, at a flow rate of 1.5 ml/minute. The buffer of this chromatography peak was exchanged by medium-pressure chromatography using a Hi Trap Desalting column. The conditions were 10 mM sodium phosphate buffer-120 mM sodium chloride buffer (pH 7.4), flow rate 1 ml/minute.

EXAMPLE 10

Immunosuppressive Activity of the Recombinant MAY-I, H4P and Partial-H4P Prepared in Example 9

Figure 9:
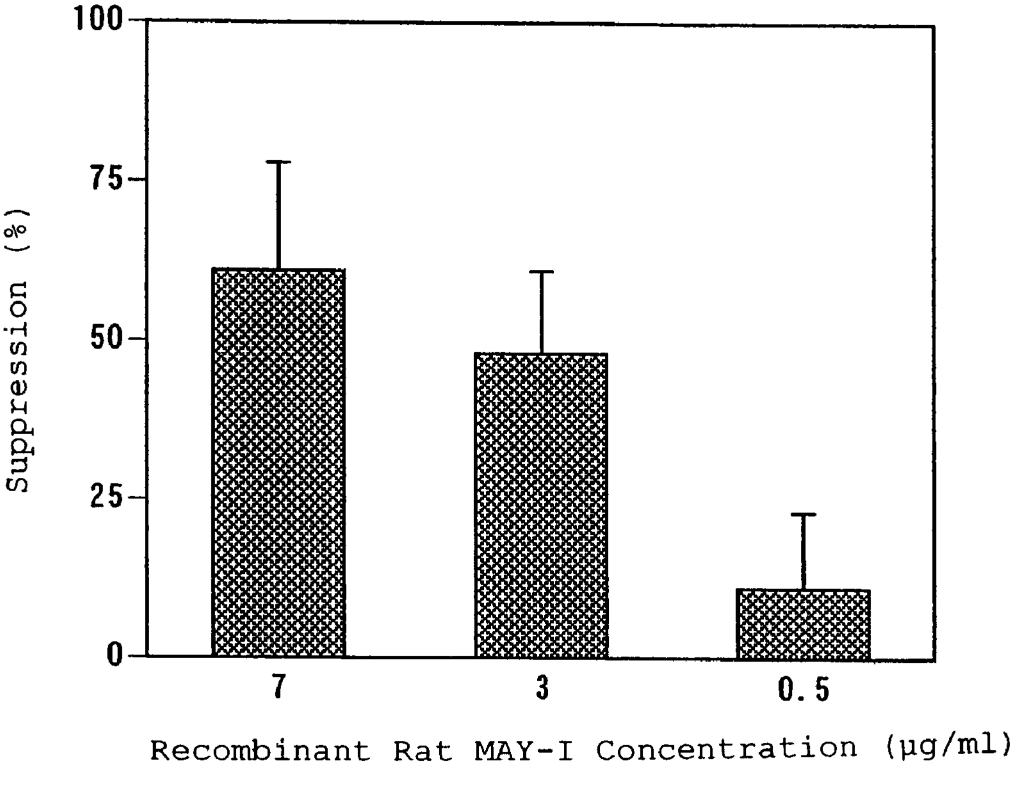
FIG. 9 shows the immunosuppressive activity in allogeneic rat MLR of recombinant rat MAY-I.
Figure 10:
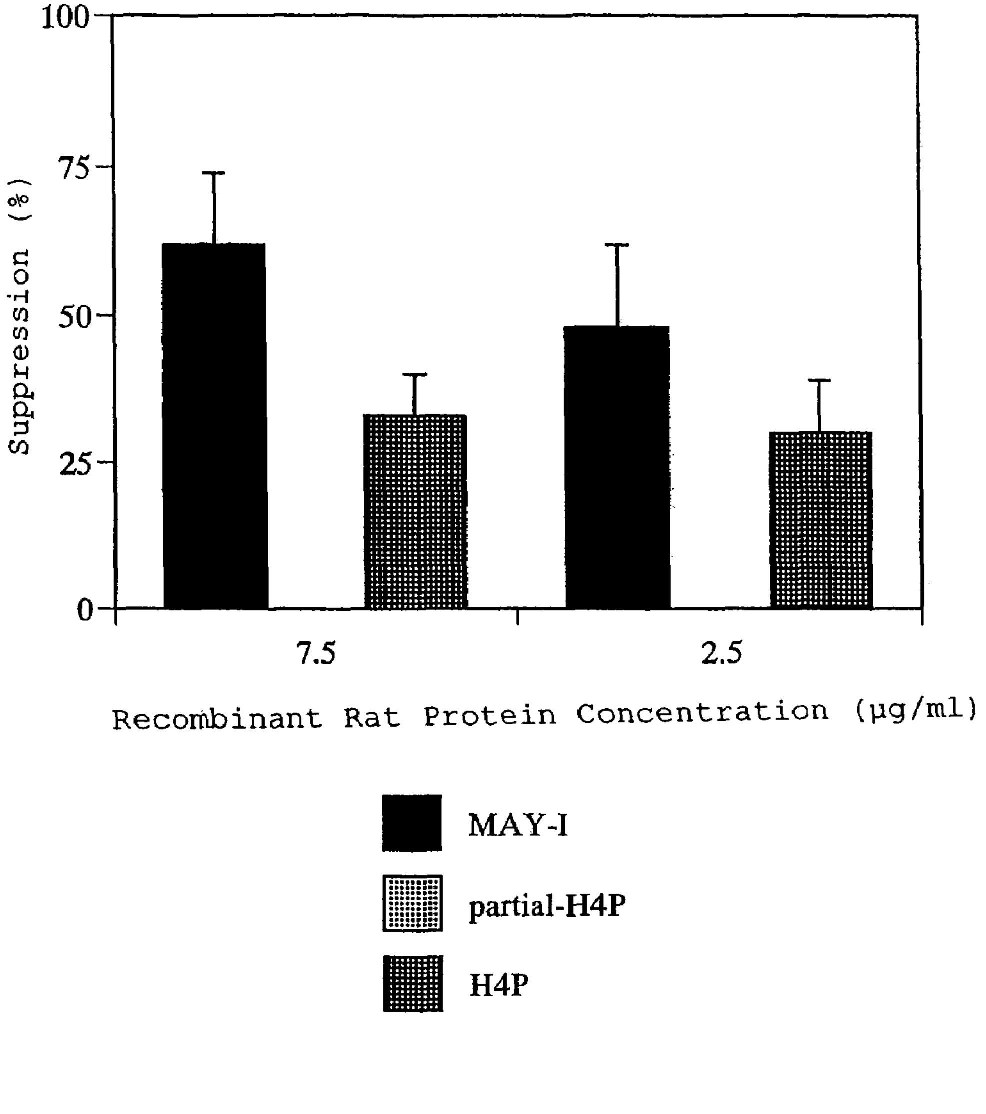
FIG. 10 shows the immunosuppressive activity in allogeneic rat MLR of recombinant rat MAY-I, IαIH4P and partial-H4P.

The immunosuppressive activity in allogeneic rat MLR of the recombinant MAY-I (SEQ ID NO:1) prepared in Example 9 was investigated as in Example 1, and concentration-dependent immunosuppressive activity was shown (FIG. 9). When the immunosuppressive activity of the recombinant H4P (SEQ ID NO:8) and partial H4P was investigated in the same way, the former exhibited immunosuppressive activity but the latter did not (FIG. 10). These results confirm that MAY-I controls immunosuppressive activity.

EXAMPLE 11

Cloning of DNA Encoding Human MAY-I (1)

Total RNA was prepared from Hep G2 cells using Isogen (Nippon Gene) according to the manual. Using a 6-base random primer (TAKARA), cDNA was synthesized from the resulting 10 μg of total RNA with M-MLV reverse transcriptase (GIBCO BRL). PCR was performed using 1 μg of the synthesized cDNA as a template. The nucleotide sequences shown by (SEQ ID Nos. 29 and 30 were synthesized as the PCR primers. For the PCR reaction, the template DNA was first thoroughly denatured by 1 minute of heat treatment at 95° C., then a cycle of 30 seconds at 95° C. and 1 minute at 68° C. was repeated 25 times, followed by a 10-minute elongation reaction at 68° C. Following agarose gel electrophoresis, the amplified DNA fragment was collected from the gel, digested with restriction enzymes BamH I and Xho I, cloned to the BamH I and Xho I sites of protein expression vector pScc Tag2 B (Invitrogen), and introduced into *E. coli* DH5α to obtain *E. coli* DH5α/Human MAY I-pSec Tag2 B. After the nucleotide sequence of the inserted cDNA was confirmed as in Example 7, a cDNA sequence (SEQ ID NO:15) encoding the protein (human MAY-I) from amino acid 661 through the C-terminal amino acid of human IHRP was obtained.

EXAMPLE 12

Cloning of DNA Encoding Human MAY-I (2)

A transformant containing cDNA homologous to DNA encoding rat MAY-I was cloned from a human liver cDNA library (Clontech), using DNA encoding rat MAY-I as the probe. Analysis of the nucleotide sequence of this cDNA fragment confirmed that the cDNA fragment included the coding regions between base 1424 and the C-terminal of the human IHRP cDNA sequence (SEQ ID NO:16).

EXAMPLE 13

Figure 11:
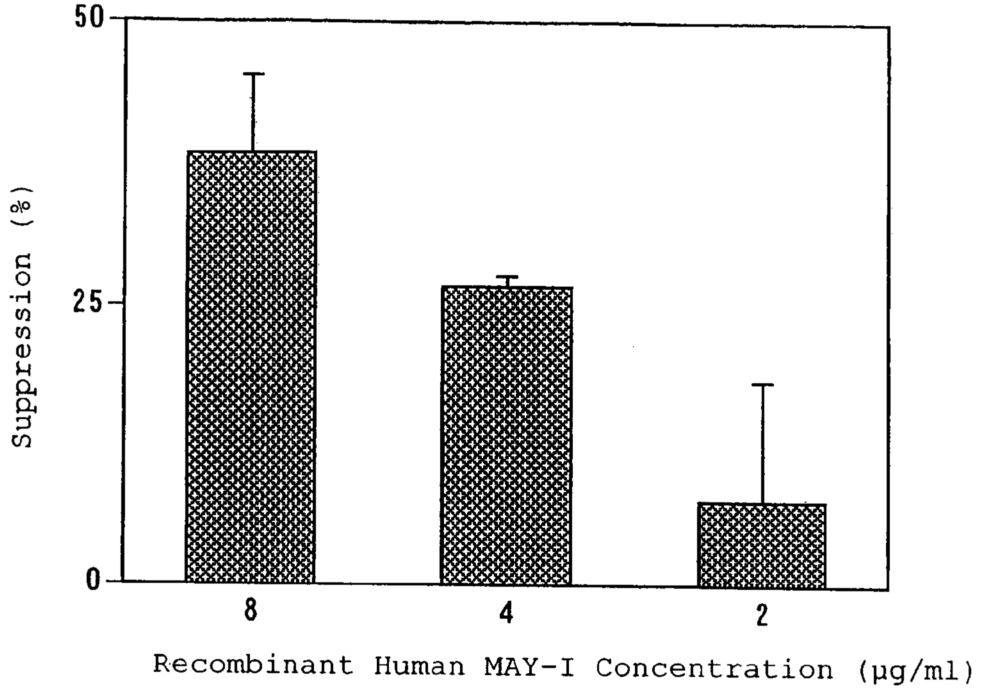
FIG. 11 shows the immunosuppressive activity in allogeneic human MLR of recombinant human MAY-I.

Preparation of Protein (Human MAY-I) Obtained in Example 11 Corresponding to Amino Acids Between 661 and the C-terminal of Human IHRP, and Immunosuppressive Activity of Prepared Recombinant Human MAY-I The Human MAY I-pSec Tag2 B prepared in Example 11 was transfected into COS 7 cells by the DEAE Dextran method. The day after transfection it was transferred to FBS-free medium and cultured for 24 hours, after which the culture supernatant was collected and recombinant Human May-I therein isolated and purified according to the methods shown in Example 9. This Human MAY-I exhibited concentration-dependent immunosuppressive activity in human MLR (FIG. 11).

INDUSTRIAL APPLICABILITY

Since the protein of the present invention has immunosuppressive activity, it is useful as a prophylactic or therapeutic agent for auto-immune disorders (rheumatism, psoriasis and the like) or allergic disorders (allergic asthma (bronchial asthma), allergic rhinitis, allergic conjunctivitis, allergic dermatitis (atopic dermatitis), pollinosis and the like), and antirejection drug.

The invention claimed is:

1. An isolated protein having immunosuppressive activity, said protein consisting of an amino acid sequence having 95%–100% identity with the amino acid sequence shown by SEQ ID NO:14.

2. A medicinal composition containing, as an active ingredient, an isolated protein having immunosuppressive activity, said protein consisting of an amino acid sequence having 95%–100% identity with the amino acid sequence shown by SEQ ID NO:14, together with a pharmacologically acceptable carrier.

3. A method of causing immunosuppression in a human comprising administering a composition according to claim 2 to the human in need thereof.

4. The method as defined in claim 3, wherein the immunosuppression is for treatment of an auto-immune disorder or allergic disorder, or for suppressing rejection.

5. The method as defined in claim 4, wherein the allergic disorder is bronchial asthma, allergic rhinitis, allergic dermatitis or pollinosis.

* * * * *

UNITED STATES PATENT AND TRADEMARK OFFICE

CERTIFICATE OF CORRECTION

PATENT NO. : 7,091,316 B2 
APPLICATION NO. : 10/344307
DATED : August 15, 2006
INVENTOR(S) : Hiroo Uchida et al.

It is certified that error appears in the above-identified patent and that said Letters Patent is hereby corrected as shown below:

Column 1, Line 4 below the TITLE insert

-- This application is the U.S. National Phase under 35 U.S.C. §371 of International Application PCT/JP01/06620, filed August 1, 2001, which claims priority to Japanese Patent Application No. 2000-241169, filed August 9, 2000. The International Application was published under PCT Aricle 21 (2) in a language other than English.--.

Column 68, Line 25, (approx) in Claim 4, delete

“an auto-immune disorder” and insert -- rheumatism, psoriasis --, therefore.

Signed and Sealed this

Twenty-sixth Day of December, 2006

JON W. DUDAS
*Director of the United States Patent and Trademark Office*